United States Patent [19]

Relyveld

[11] 4,075,321

[45] Feb. 21, 1978

[54] VACCINES, THE PROCESS FOR PREPARING THE SAME AND THE APPLICATIONS THEREOF

[75] Inventor: Edgar Hans Relyveld, Paris, France

[73] Assignee: Agence Nationale de Valorisation de la Recherche (ANVAR), Neuilly-sur-Seine, France

[21] Appl. No.: 704,706

[22] Filed: July 12, 1976

Related U.S. Application Data

[62] Division of Ser. No. 465,712, April 30, 1974, Pat. No. 3,983,229.

[30] Foreign Application Priority Data

May 4, 1973 France .................................. 73.16131

[51] Int. Cl.$^2$ .............................................. A61K 39/02
[52] U.S. Cl. .................................................... 424/92
[58] Field of Search ..................................... 424/88–92

[56] References Cited

U.S. PATENT DOCUMENTS

| 3,135,662 | 6/1964 | Pope et al. ............................. 424/92 |
| 3,608,071 | 9/1971 | Relyveld et al. ...................... 424/88 |
| 3,761,585 | 9/1973 | Mullan et al. .......................... 424/91 |
| 3,794,630 | 2/1974 | Mullan et al. ..................... 260/112 R |
| 3,925,545 | 12/1975 | Relyveld ............................... 424/92 |
| 3,983,229 | 9/1976 | Relyveld ............................... 424/92 |

FOREIGN PATENT DOCUMENTS 2,421,083   11/1974   Germany .................................. 195/80

OTHER PUBLICATIONS

Hughes et al., Biochem. J. 119:925–926 (1970) "Cross--Linking of Bacterial Cell Walls with Glutaraldehyde".
Eskenazy, Nature 226:855–856, May 30, 1970, "Isolation of Anti-Polysaccharide Antibodies with Glutaraldehyde Cross-Linked Lipo Polysaccharides".
Chem. Abstr. (C.A.) 64, No. 1050b (1966).
C.A. 67, No. 1795h (1967).
C.A. 70, No. 66297d (1969).
C.A. 70: 104623s, 104624t, 104625u (1969).
C.A. 71, No. 20570e (1969).
C.A. 79, No. 135223b (1973).
C.A. 82, No. 123221y (1975) of Ger. Offen. 2,421,083, Nov. 21, 1974.
C.A. 82, No. 65364e (1975) of Relyveld, Girard, Desor Meau–Bidot Ann. Immunol. Hung. 17:21–31 (1973) Preparation of Vaccines Using Glutaraldehyde.

Primary Examiner—Shep K. Rose
Attorney, Agent, or Firm—Burgess, Dinklage & Sprung

[57] ABSTRACT

This invention relates to a process for preparing vaccines, which consists in bringing into contact a toxic product with glutaraldehyde at a concentration and for a duration just sufficient to detoxify or inactivate said toxic product, and in stopping the glutaraldehyde-antigen reaction as soon as said inactivation stage is reached by physical and/or chemical means. The thus obtained inactivate product remaining antigenic and retaining its immunizing power, is usable as a vaccine for the preventive treatment of human and animals against infections caused for example by microbial or venomous toxins.

26 Claims, No Drawings

VACCINES, THE PROCESS FOR PREPARING THE SAME AND THE APPLICATIONS THEREOF

This is a division of application Ser. No. 465,712, filed Apr. 30, 1974 now U.S. Pat. No. 3,983,229.

The present invention, which is the outcome of labours carried out at the Pasteur Institute, relates to the field of immunization. More particularly, this invention relates notably to new vaccines, the process for preparing the same and the applications thereof in the prevention of diseases, as well as the hyperimmune sera prepared by the use of said new vaccines.

It is known that formaldehyde is the agent most frequently used for converting a toxin into an anatoxin. Said compound is used in the form of formol, i.e. an aqueous solution of formaldehyde. The known process consists in incubating the toxin in the presence of formol at temperatures of 35°–40° C for a period of 2 to 6 weeks. The toxin is thus inactivated, so making it possible to manufacture the corresponding vaccines.

This known process cannot be used to prepare vaccines from all the known toxins. For example, it is not suited to prepare vaccines from snake venom.

The inactivation period using formol is long.

It is also desirable to discover a process for preparing efficacious vaccines more rapidly.

The micro-organisms used as antigens for preparing vaccines are generally inactivated by heat, formalin, phenol or a combination of said means. Said known processes sometimes denature the protective antigens. In certain cases, therefore, this results in a loss of the specificity in the immunological response of the vaccinated subject.

Formol (polio), β-propiolactone (polio), UV radiation (herpes), or the combined action of chemical and physical agents, are generally used to inactivate viruses. The polio virus, for example, is inactivated with formol and then is treated with β-propiolactone.

These processes for inactivating antigens in view of the preparation of vaccines gave good results for certain viruses, such as those of poliomyelitis and rabies, but cannot be generalized to all the viruses which are agents of infectious diseases of man and animals; for example, the vaccines against foot-and-mouth disease, hitherto prepared, only confer immunity for a fairly short period of time, and yearly vaccinations are therefore necessary. Finally, it has never been possible to prepare a well-tolerated vaccine efficacious against the toxins of poisonous snakes. At present, the sole treatment for poisonous snake bites is serotherapy.

It is frequently still necessary to introduce various adjuvants into the vaccine composition, for instance, inorganic compounds, such as aluminum hydroxide or calcium phosphate.

The object of the present invention is a general means for preparing vaccines, the vaccines obtained and the application thereof in preventive treatments of men and animals.

Another object of this invention is a process, which allows the preparation of vaccines in a very short time, for example in the range of from one minute to a few hours, in the case of micro-organisms and their toxins.

Still another object of this invention is a process for preparing vaccines enabling the anatoxin to be obtained with a greater efficiency or yield than known processes.

A further object of this invention is a process for preparing new vaccines, particularly vaccines efficacious against the micro-organisms responsible for catching diseases, microbial toxins and those of poisonous snakes.

A still further object of this invention is a process enabling viral vaccines to be obtained, certain of which are new, and in a period of a few days.

Yet another object of this invention is a process for producing vaccines in the presence, or the absence, of the conventional adjuvants, such as aluminum hydroxide or phosphate or calcium phosphate.

Another object of this invention in the provision of hyperimmune sera prepared by using the new vaccines, the sera being administered to men and animals in preventive or curative treatments.

In its most general form, the invention includes process for preparing various vaccines, which consists in contacting the toxic product with glutaraldehyde at a concentration and for a length of time just sufficient to detoxify or inactivate the said toxic product, and in stopping the reaction, as soon as the detoxification or inactivation stage is reached, by physical and/or chemical means, the inactivated product obtained being usable as a vaccine while remaining antigenic and retaining its immunizing properties.

It is generally known that aldehydes have a detoxifying activity, and the use of glutaraldehyde as a disinfectant has already been proposed. But, in the field of immunization, it is not enough to obtain a detoxified product in order that it is actually usable as a vaccine. It is necessary to elaborate conditions for the industrial manufacture of the vaccine providing all the guarantees of efficacy, reproducibility, innocuity and stability.

According to this invention, the treatment with glutaraldehyde is effected under controlled conditions and, according to a fundamental characteristics of the process, the reaction is stopped so as to remove the toxicity of the initial product, without its being denatured, that is to say, it retains its antigenic character.

To control the treatment, preliminary trials are effected with the toxic product in question. One skilled in that art possesses objective means of determining in a given system the glutaraldehyde concentration and duration of treatment, efficacious to detoxify the product. For example, if toxins are treated, it is necessary not only to follow detoxification in the animal, but also to observe the titer of the treated product in flocculation units per volume units (FU/ml) and the time of flocculation (Kf). Thus, if no further flocculation is observed in the medium during treatment, it is certain that the detoxified product has been denatured. It is therefore necessary, to observe the loss or lowering of the titer (FU/ml) on the one hand, and the increase in the flocculation time (Kf) on the other hand. These two elements of observation enable the desired duration of contact of glutaraldehyde with the toxic product, for a given concentration of glutaraldehyde, and vice-versa, t be determined.

This invention proposes a certain number of means, used alone or in combination, for stopping the reaction as soon as the product has been detoxified. A first means for stopping the reaction consists in removing the excess of glutaraldehyde chemically by adding to the reaction mixture a chemical agent able to react with the free glutaraldehyde. Among the various chemical agents able to react with aldehydes, the amino acids, such as lysine or glycin, or inorganic salts, such as sodium bisulphite, are preferably used. As example, an aqueous lysine solution of pH between about 7 and 8 can be used.

Another method for removing the excess of glutaraldehyde from the reaction mixture consists in using physical means, particularly by dialyzing the medium against a buffer solution, such as a sodium phosphate or chloride buffer. In the case of the treatment of germs with glutaraldehyde, another method consists in centrifuging the germs and washing them to remove the excess of glutaraldehyde. In this case, it may be advantageous to select a concentration of glutaraldehyde corresponding to a duration of detoxifying treatment, compatible with the duration of the washing centrifuging operation.

It will also be pointed out that the products detoxified by the glutaraldehyde treatment according to this invention, can be directly used as vaccines in a fluid form. However, it is also possible to prepare vaccines in an adsorbed form, when a calcium chloride solution is added to the fluid vaccine, obtained, for example, by dialysis against a buffer solution, such as a sodium phosphate buffer, a calcium chloride solution or, when aluminum hydroxide or phosphate is added to the liquid vaccine, obtained by dialysis against a sodium chloride solution; a vaccine adsorbed on the conventional adjuvants (aluminum hydroxide, calcium phosphate, etc.) is thus obtained.

The vaccines according to this invention are characterized in that the glutaraldehyde molecules have reacted with the toxic product.

In this connection glutaraldehyde acts in a manner fundamentally different from formaldhyde. Glutaaldehyde is a bifunctional reagent able to simultaneously detoxify the toxic starting product and inducing cross-linking or bridging reactions on the molecules of said product.

Studies were effected to characterize the products resulting from the reaction of glutaraldehyde and the toxic product. Said studies involved flowing through a column and ultracentrifugation of various products. In the case of the diphtherial toxin for example, it was shown that the native toxin comprised essentially monomer products, the percentage of dimers being lower than about 10%. In the case of a toxification treatment of said diphtherial toxin by formaldehyde, it is found that the reaction product is essentially monomer, the solution containing substantially no dimers in the limits of about 3 to 5%. According to the process of this invention, i.e. the treatment of the diphtherial toxin by glutaralhyde, the reaction product consists substantially of highly aggregated molecules of variable molecular weight. The residual amount of monomer products is in the range of about 5 to 10%.

According to this invention, no formation of a precipitate in the liquid reaction mixture is observed, as it would be the case if a high molecular weight polymer were formed. Said property is of critical importance, as it is due to the hereinabove described controlled reaction conditions. Owing to the fact that the reaction of glutaraldehyde and toxic product is stopped as soon as detoxification is obtained, the detoxified product remains efficacious as a vaccine whereas, if the reaction were carried on, it would form compounds, which would not have the desired immunizing power.

Thus it is not desirable to carry on the detoxification reaction beyond a threshold, which can be determined each time with regard to the treated toxic product and the conditions of treatment, i.e. essentially the concentration of the glutaraldehyde solution and the duration of treatment.

In the prior art, glutaraldehyde has already been proposed, for example to inactivate viruses, i.e., to prevent their development (see, for example, Fred L. SABEL and al, Applied Microbiology, April 1969, p. 645–646, Vol. 17, No. 4).

The conditions, under which these known processes are carried out do not enable the immunological properties of the initial virus to be retained. For example, in the article by SABEL and al, the concentration of glutaraldehyde is as high 5% by weight of the reaction mixture, it is a value at which the immunological properties of the viruses disappeared.

According to this invention, on the contrary, the glutaraldehyde treatment is carried out under controlled conditions adapted to vaccine preparation. It is indeed necessary to obtain a viral strain which has lost its properties of multiplication but has retained its vaccinal antigenic structures. According to the fundamental characteristic of the invention, the reaction between glutaraldehyde and the treated product is stoped at a controlled moment, whereby the toxicity of the initial product is removed without its being denatured.

While in no way being bound to a theoretical explanation, it is thought that under the conditions of the reaction carried cut according to this invention, glutaraldehyde induces a limited cross-linking or polymerization reaction between the molecules of toxic products, so as to obtain a detoxified product validly usable as a vaccine.

Within the meaning of the present disclosure, the term "toxic product" refers to microbial or venomous toxins, cultures or suspension of micro-organisms, germs, bacteria and viruses. Thus, the vaccines of this invention can be prepared from various toxins or mixtures of said microbial or venomous toxins, and also from a very wide range of germs, bacteria, viruses and microorganisms.

As an example, it is notably possible according to this invention to prepare vaccines from diphtherial, tetanic and $\alpha$ and $\beta$ staphylococcus toxins, snake venoms and any other microbial or venomous toxins, such as staphylococcus or whooping-cough-(bacteria) or poliomyelitis virus and foot-and-mouth disease virus. In certain cases, mixed vaccines may be obtained insofar as a mixture of toxins, or microbial infectious agents (bacteria, virus and the like) are inactivated by the process of the invention. As example, there may thus be prepared a mixed antidiphtherial-antitetanic vaccine.

In the case of the diphtherial toxin, it is advantageous to effect the treatment with glutaraldehyde and stop the reaction by adding an amino-acid, such as lysine or glycin. The fluid product, obtained by treatment with glutaraldehyde, can also be subjected to a dialysis against a phosphate buffer solution, thus obtaining a product, which can also be used as a vaccine, and which contains anatoxins in the adsorbed form, after precipitation of the phosphate ions by means of calcium. It is advantageous to add, to the buffer solution, a substance for preventing contamination, such as merthiolate.

In the case of tetanic toxin, it is also possible to prepare a fluid vaccine containing anatoxins or a vaccine in the adsorbed form.

In the case of crude or purified $\alpha$-staphylococcus toxin, it is also possible to effect the glutaraldehyde treatment and submit the obtained product to the action of lysine, glycin or to dialysis against a sodium chloride buffer solution, added with merthiolate.

In the case of the detoxification of venoms, vaccines are obtained by treatment with glutaraldehyde, advantageously followed by a dialysis or an addition of an amino acid. The following procedure can be used to prepare the vaccine: after having added merthiolate to the liquid anavenom, the mixture is dialyzed against a 0.07 M $Na_2HPO_4$ phosphate buffer solution with merthiolate and filtered through a Seitz-type sterilizing filter, thus providing a fluid vaccine containing liquid anatoxins. This can be mixed with a sterile 0.07 M calcium chloride solution, thus providing a vaccine adsorbed on calcium phosphate the pH of which is adjusted to 6.8 – 7.00.

According to an another embodiment, it is also possible to dialyze the fluid vaccine against a sodium chloride solution, filter it and add aluminum hydroxide or diphosphate as adjuvant.

Similarly, whooping-cough vaccines can be prepared in the fluid and adsorbed form.

In the case of the inactivation of poliomyelitis viruses, it is advantageous, among other things, to adjust the glutaraldehyde concentration in order to reduce to a minimum the risk of virus denaturation.

Generally speaking, one skilled in the art has at his disposal a certain number of factors, which can be varied in order to obtain efficacious and satisfying vaccines, and essentially the following factors: the concentration of glutaraldehyde, the time of contact with the toxic product, the nature of said toxic product; the purity of the toxic product can also play a part, as well as the temperature of treatment, although it is generally approximately ambient temperature or in the range of 35°–40° C, notably 37° C.

It goes without saying that, among the factors which have an influence on the control of the process, the physical and chemical means enabling the reaction of glutaraldehyde on the toxic product be be stopped, should also be taken into account. Throughout the present disclosure, notably where the detailed embodiments of the process are described, when the times of contact or incubation are mentioned, this means the exact duration of contact between the glutaraldehyde and the toxic product, the reaction being stopped immediately after the given time by at least one of the hereinabove described physical or chemical means As it was hereinabove pointed out, an advantageous method for controlling the proper toxicity of glutaraldehyde consists in carrying out the inactivation treatment by means of glutaraldehyde and in adding lysine to the reaction medium. Lysine is an advantageous representative example of an amino-acid or equivalent chemical agent able to block the glutaraldehyde-antigen reaction.

The process of the present invention provides atoxic derivatives for use as fluid vaccines, having a high immunizing power, such as fluid vaccines, which can be used as they are or in the presence of the conventional adjuvants (aluminum hydroxide or phosphate, calcium phosphate, oil-water mixtures etc.).

From another point of view, the invention also relates to the hyperimmune sera obtained by taking samples from man or an animal, such as the horse, donkey or goat, to whom a vaccine according to the invention is administered at short time intervals in accordance with the conventional immumization methods. Said sera can be used, in a known manner, on man and animals for the preventive and curative treatment of infections caused by microorganisms or their derivatives corresponding to the vaccine administered. Said sera are also applicable as diagnostic products.

The following description deals more particularly with the action of glutaraldehyde at variable concentrations based on the time of contact, at 37° C, on toxins at various stages of purification, on bacteria, venoms and viruses.

The following disclosure concerns, successively:

A — diphtherial toxin
B — tetanic toxin
C — crude $\alpha$ staphylococcal toxin
D — purified $\alpha$ staphylococcal toxin
E — crude $\beta$ staphylococcal toxin
F — purified $\beta$ staphylococcal toxin
G — venoms of Aspis, Berus and Ammodytes vipers and other snakes
H — staphylococcal germs
I — whooping-cough bacillus
J — poliomyelitius viruses
K — foot-and-mouth disease viruses The immunogenic power of the derivatives was also studied in a certain number of cases.

In paragraph L, the proper toxicity of glutaraldehyde is studied. Finally, in paragraph M the preparation of a mixed antitetanic-antidiphtherial vaccine is illustrated.

The molar concentrations of used glutaraldehyde were as follows:

0.0263 M = 10.7 ml of glutaraldehyde per liter (25% solution)
0.00263 M = 1.07 ml of glutaraldehyde per liter
0.0526 M = 21.4 ml of glutaraldehyde per liter
0.00526 M = 2.14 ml of glutaraldehyde per liter.

A certain number of different concentrations were also studied, notably, weaker concentrations up to 0.00131 M or less, according to the type of treated toxic product.

The following detailed disclosure shows the influence of various factors on the reaction between the toxic product and glutaraldehyde, and illustrates the means for controlling the reaction, according to the process of the invention.

The following abbreviations will be used to designate the reactions observed on laboratory animals:

Er — Erythema
Es — Eschar
ES → cic Eschar in process of cicatrization
Cis — ES Cicatrized eschar
SES — Small eschar
$SE_r$ — *Small erythema*
ES tr — Eschar traces
SI — Slight induration
VSI — Very slight induration
SL Slight reaction in the form of an erythema
VSL — Very slight reaction in the form of an erythema
N — Nodule
Ntr — Nodule traces
SN — Small nodule
tr — traces
NTR — Nothing to report
Nd — no-dilued.

The following description also contains the below abbreviations:

FU — Flocculation units
IAU — International antitoxic units

MHD — Minimum hemolytic dose
CHD — Combined hemolytic dose

A. Study of the detoxification of diphtherial toxin

1. The action of glutaraldehyde on pure 500 FU/ml toxin

Tables 1 and 2 give the results, obtained by the action of glutaraldehyde at final concentrations of 0.0263 M and 0.00263 M.

The action of glutaraldehyde at a concentration of 0.0263 M, i,e., equal to the amount of formol usually used to detoxify said toxin during a time period of at least 2 weeks at 37° C, caused the toxin to completely lose its flocculating power after contact for 1 hour at the same temperature.

At a concentration of 0.00263 M glutaraldehyde, the obtained flocculating power was much less pronounced, but higher than the one observed with formol after a prolonged period of contact.

Experiments on the residual toxicity of the preparations on the guinea pig, show that after contact for 1 hour at a concentration of 0.00263 M, the toxin was substantially completely detoxified. After 3 hours contact, the preparation assaying 420 FU /ml no longer caused the death of the guinea pig.

The proper toxicity of glutaraldehyde is removed either by the action of lysine or by dialysis.

2. The action of glutaraldehyde on a partially purified $P_2$ type toxin.

Tables 3 and 4 give the results obtained by the action of glutaraldehyde on a partially purified 2,500 FU/ml toxin.

In this case higher concentrations of glutaraldehyde need to be used to obtain total detoxification. The preparation is completely detoxified by the action of 0.0263 M glutaraldehyde after contact for 3 hours, but at a concentration of 0.00263 remains toxic after contact for 1 week.

In this case, a decrease of the flocculating power is also observed.

3. The action of glutaraldehyde on ultrafiltered crude 4,500 FU/ml diphtherial toxin,.

Tables 5 and 6 give the results of experiments conducted with a final glutaraldehyde concentration of 0.0263 M and 0.00263 M.

It is observed, that a complete detoxification is again obtained after contact for 1 hour with the 0.0263 concentration.

The preparation is not detoxified after 2 weeks contact with the 0.00263 concentration.

4. Results of detoxification experiments on the diphtherial toxin.

Complete detoxification of the diphtherial toxin without denaturation can be obtained after contact of 1 to 3 hours, providing that the concentrations of glutaraldehyde with regard to the proteic concentration of the used preparation are respected.

It is necessary to use higher concentrations of glutaraldehyde if a crude preparation (of higher protein content) or a higher concentration of the preparation is to be detoxified.

The detoxification conditions should therefore be specified by a preliminary study. The process of the invention has the advantage of being much more rapid than the process of detoxifying by the action of formol and heat.

Preparation of diphtherial anatoxins by the action of glutaraldehyde on a pure toxin and study of their vaccinal power in the fluid or absorbed form In the following study, the influence of lysine on immunizing power was studied. It was thus possible to determine that anatoxins, detoxified by glutaraldehyde, with the reaction stopped by lysine, have a higher immunizing power than anatoxins obtained without the use of lysine.

The anatoxins obtained after 1 and 3 h incubation with 0.00623 M glutaraldehyde and with or without stabilization with lysine were studied.

Table 9 again shows that the preparations are not completely detoxified after contact for 1 hour. After contact for 3 hours, eschare form on the animals, tested with the preparation without lysine; said reactions are certainly due to the presence of free glutaraldehyde, they are not observed after interaction with lysine.

These observations are confirmed by research into the dermonecrotic toxicity of the same anatoxins following dialysis (see table 10)

This time, similar reactions are observed with the preparations after contact for 3 hours (absence of free lysine). A slight reaction is observed with undiluted preparations, certainly due to irritation.

The preparations obtained after contact for 1 hour are toxic.

TABLE 1

Detoxification of pure 500 FU/ml diphtherial toxin by the action of glutaraldehyde at a final concentration of 0.0263 M

| Time of contact at 37° C | FU/ml | Kf | Innocuity test on the guinea pig* Observations after 24 h | 48 h | 72 h | 1 week | 2 weeks | 3 weeks | 4 weeks |
|---|---|---|---|---|---|---|---|---|---|
| 1' | 470 | 1' | — | — | — | — | — | — | — |
| 1 h | does not | — | ES | ES | ES | ES | $ES_{cic.}$→ | ES | $ES_{cis.}$→ |
| | flocculate | | ES | ES | ES | ES | $ES_{cic.}$→ | ES | $ES_{cic}$ |
| 3 h | does not | — | NTR | NTR | tr | NTR | NTR | NTR | NTR |
| | flocculate | | NTR | SES | SES | EStr | $EStr_{cic}$→ | N | NTR |
| 6 h | does not | — | SES | ES | ES | ES | $ES_{cic.}$→ | ES | $ES_{cic.}$ |
| | flocculate | | NTR | NTR | NTR | NTR | NTR | NTR | NTR |
| 24 h | does not | — | SES | ES | ES | ES | $ES_{cic}$→ | ES | $ES_{cic}$ |
| | | | NTR | SES | SES | SN | NTR | NTR | NTR |
| 1 week | does not | — | NTR | NTR | NTR | NTR | dead | | |
| | flocculate | | NTR | ES | ES | ES | ES | dead | |

*subcutaneous injection of 0.5 ml to two 250 g guinea pigs

TABLE 2

Detoxification of a pure 500 FU/ml diphtherial toxin by the action of glutaraldehyde at a final concentration of 0.00263 M

| Time of contact at 37° C | FU/ml | Kf | \multicolumn{7}{c}{Innocuity test on the guinea pig observations after} | | | | | | |
|---|---|---|---|---|---|---|---|---|---|
| | | | 24 h | 48 h | 72 h | 1 week | 2 weeks | 3 weeks | 4 weeks |
| 1' | 500 | 1' | — | — | — | — | — | — | — |
| 1 h | 450 | 6' | ES SL | SL ES SL | SL SES VSL | SES tr | tr EScic NTR | ES NTR | dead dead |
| 3 h | 420 | 9' | NTR SL SES | NTR SL tr ES | NTR tr | NTR NTR | NTR NTR | NTR NTR | NTR NTR |
| 6 h | 400 | 16' | SL SE, | NTR tr | NTR tr | NTR NTR | NTR NTR | NTR SN | NTR NTR |
| 24 h | 350 | 1h 20 | NTR VSL | NTR tr | NTR NTR | NTR NTR | NTR NTR | NTR NTR | NTR ill* |
| 48 h | 330 | 2h 05 | NTR NTR | NTR NTR | NTR NTR | NTR NTR | NTR NTR | NTR NTR | NTR NTR |
| 1 week | 325 fine precipitate | >3h | ill NTR | NTR NTR | NTR NTR | NTR NTR | ill NTR | dead NTR | |
| 2 weeks | 225 fine precipitate | >7h | NTR NTR | NTR NTR | NTR NTR | NTR NTR | NTR NTR | | |

*ill = ill

TABLE 3

Detoxification of partially purified 2500 FU/ml diphtherial toxin (P₂) by the action of glutaraldehyde at a final concentration of 0.0263 M

| Time of contact at 37° C | Flocculation before dialysis | | \multicolumn{6}{c}{Inocuity test on the guinea pig* observations after} | | | | | |
|---|---|---|---|---|---|---|---|---|
| | FU/ml | Kf | 24 h | 48 h | 72 h | 1 week | 2 weeks | 3 weeks |
| 1' | 2,400 | 3' | — | — | — | — | — | — |
| 3 h | 1,450 | 50' | NTR NTR | NTR NTR | NTR NTR | NTR NTR | NTR NTR | NTR NTR |
| 24 h | 1,400 | 5 h | NTR NTR | NTR NTR | NTR NTR | dead NTR | NTR | NTR |
| 3 days | 1,250 fine precipitate | 24 h | NTR NTR | NTR NTR | NTR NTR | NTR NTR | NTR NTR | NTR NTR |
| 1 week | 1,000 cloudy | 24 h | NTR NTR | NTR NTR | NTR NTR | NTR NTR | NTR NTR | NTR NTR |

*subcutaneous injection of 0.5 ml to two 250 g guinea pigs after dilution to 1/10 with a sterile 9‰ NaCl solution.

TABLE 4

Detoxification of partially purified 2500 FU/ml diphtherial toxin by the action of glutaraldehyde at a final concentration of 0.00263 M

| Time of contact at 37° C | Flocculation before dialysis against K/K₂ M/15 buffer | | Flocculation after dialysis against K/K₂ buffer | | Innocuity test on the guinea pig |
|---|---|---|---|---|---|
| | FU/ml | Kf | FU/ml | Kf | |
| 1' | 2,400 | 2' | | | |
| 3 h | 2,250 | 3' | 2,125 | 4' | dead 24 h after the injection |
| 24 h | 2,125 | 3 | 2,125 | 4' | dead 24 h after the injection |
| 3 days | 2,100 | 7' | 2,100 | 4' | dead 24 h after the injection |
| 1 week | 1,850 | 10' | 1,850 | 5' | dead 24 h after the injection |

TABLE 5

Detoxification of ultrafilter crude 4500 FU/ml diphtherial toxin by the action of glutaraldehyde at a final concentration of 0.0263 M

| Time of contact at 37° | FU/ml | Kf | \multicolumn{5}{c}{Innocuity test on the guinea pig* observation after} | | | | |
|---|---|---|---|---|---|---|---|
| | | | 24 h | 48 h | 72 h | 1 week | 2 weeks |
| 1' | 4,300 | 4' | — | — | — | — | — |
| 1 h | 3,900 | 11' | NTR NTR | NTR NTR | NTR NTR | NTR NTR | NTR NTR |
| 3 h | 3,800 | 14' | NTR NTR | NTR NTR | NTR NTR | NTR NTR | NTR NTR |
| 6 h | 3,600 | 22' | NTR NTR | NTR NTR | NTR NTR | NTR NTR | NTR NTR |
| 24 h | 3,375 | 35' | NTR NTR | NTR NTR | NTR NTR | NTR NTR | |
| 1 week | 3,000 | 3 h | NTR NTR | NTR NTR | NTR NTR | dead | |
| 2 weeks | 2,820 | 2 h 30 | NTR NTR | NTR NTR | NTR NTR | dead | |

*Subcutaneous injection of 0.5 ml to two 250 guinea pigs after dilution to 1/10 with a sterile 9‰ NaCl solution

TABLE 6

Detoxification of crude 4500 FU/ml diphtherial toxin by the action of glutaraldehyde at a final concentration of 0.00263 M

| Time of contact at 37° C | FU/ml | Kf | Innocuity test on the guinea pig |
|---|---|---|---|
| 1' | 4,500 | 3' | |
| 1 h | 4,500 | 4' | dead 24 h after the injection |
| 3 h | 4,500 | 4' | dead 24 h after the injection |
| 6 h | 4,500 | 4' | dead 24 h after the injection |
| 24 h | 3,800 | 4' | dead 24 h after the injection |
| 1 week | 3,250 | 5' | dead 24 h after the injection |
| 2 weeks | 3,150 | 3' | dead 24 h after the injection |

TABLE 9

Preparation of an anatoxin by the action of glutaraldehyde at a
final concentration of 0.00263 M
1 - Controls before Dialysis

| Time of contact at 37° C | FU/ml | Kf | \multicolumn{5}{c}{Innocuity test on the guinea pig observations after} |
|---|---|---|---|---|---|---|---|
| | | | 24 h | 48 h | 1 week | 2 weeks | 3 weeks |
| 1' | 520 | 1'30 | — | — | — | — | — |
| 1 h | 500 | 4' | ES SI | ES SI | dead | | |
| | | | SL SI | SI | dead | | |
| 1 h + lysine 0.01 M 15' | 475 | 4'30 | NTR SL SI | SN VSL | N N | NTR dead | NTR |
| 3 h | 450 | 7' | VSL SL SI | SI SI ES | ES ES | ES ES | ES cic. ES cic. |
| 3 h + lysine 0.01M 15' | 430 | 8' | NTR NTR | ES VSI | NTR NTR | NTR NTR | NTR NTR |

TABLE 10

Preparation of an anatoxin by the action of glutaraldehyde at a final concentration of 0.00263 M
2 - Controls after dialysis against a 0.07 M $Na_2HPO_4$ solution + merthiolate 1 : 10,000

| Time of contact at 37° C | Before dialysis volume in ml | Fu/ml | after dialysis volume in ml | FU/ml | \multicolumn{3}{c}{Dermonectoric toxicity in the rabbit*} |
|---|---|---|---|---|---|---|---|
| 1 h | 30 | 500 | 28.6 | 450 | Nd | >20 | >20 PES |
| | | | | | 1/10 | 16 | 18 |
| | | | | | 1/100 | 0 | 0 |
| | | | | | 1/1000 | 0 | 0 |
| 1 h + lysine 0.01 M 15' | 30 | 475 | 27.5 | 440 | Nd | >20ES | >20ES |
| | | | | | 1/10 | >20 | >20 |
| | | | | | 1/100 | 12 | 16 |
| | | | | | 1/1000 | 0 | 0 |
| 3 h | 30 | 450 | 27.5 | 430 | Nd | 12 | 9 |
| | | | | | 1/10 | 0 | 0 |
| | | | | | 1/100 | 0 | 0 |
| | | | | | 1/1000 | 0 | 0 |
| 3h + lysine 0.01M 15' | 30 | 430 | 28.1 | 420 | Nd | 14 | no dif. |
| | | | | | 1/10 | 0 | 0 |
| | | | | | 1/100 | 0 | 0 |
| | | | | | 1/1000 | 0 | 0 |

*Intradermic injection of 0.1 ml to two white male rabbits. Reactions are determined 48 hours after the injection.

Tables 11 to 14 show that the weight evolution of vaccinated animals is normal with the four types of anatoxins (adsorbed and non-adsorbed). An erytherma or nodule is observed on animals, vaccinated with the adsorbed vaccine; this is absolutely normal.

On the whole, the four vaccines are perfectly well tolerated; no deaths occurred during the observation period.

Table 15 gives the titer of the circulating antibodies in International Units. The adsorbed vaccines have a higher immunological activity than fluid vaccines.

The adsorbed anatoxin, obtained by stopping the reaction by lysine, gives the best immunological response.

Weight evolution and tolerance in the guinea pig, vaccinated with two injections, at 15 days internal, with:
the fluid anatoxin (obtained without the use of lysine)
the fluid anatoxin (obtained with the use of lysine)
adsorbed anatoxin (obtained without the use of lysine)
adsorbed anatoxin (obtained with the use of lysine)

Study of the vaccinal power of fluid anatoxins obtained by the action of 0.0263 M glutaraldehyde after various times of contact on a partially purified 2000 UF/ml diphtherial toxin ($P_2$)

Table 16 shows again that, at 37° C, the loss of flocculating titer increases with the length of contact.

The different anatoxins were diluted to 30 FU/ml, based on the starting titer, and injected to guinea pigs in the fluid form.

Table 17 shows that the level of antibodies, obtained after said vaccinations decreases after contact for 1 minute. There is therefore no derivative formation with a vaccinal power comparable with the one of the adsorbed anatoxins previously studied.

TABLE 11

30 FU/ml fluid anatoxin
obtained after 3 h contact with glutaraldehyde at a final concentration
of 0.00263 M

| 1st inj. | 24 h | 48 h | 4 days | 5 days | 2 weeks (2nd inj.) | | 3 weeks |
|---|---|---|---|---|---|---|---|
| weight comments | comments weight | comments weight | comments weight | weight comments | weight comments | | weight comments |
| 280 g. | NTR | VSI | NTR | 320 g | 330 g | | 380 g |
| 275 g. | SI | NTR | VSL | 325 g | 340 g | | 380 g |
| 300 g. | NTR | NTR | NTR | 340 g | 370 g | | 410 g |
| 280 g. | tr | VSL | VSL | 325 g | 360 g | Tr N | 420 g |
| 280 g. | NTR | NTR | NTR | 315 g | 330 g | | 360 g |

TABLE 11-continued

30 FU/ml fluid anatoxin obtained after 3 h contact with glutaraldehyde at a final concentration of 0.00263 M

| 1st inj. | 24 h | 48 h | 4 days | 5 days | 2 weeks (2nd inj.) | 3 weeks |
|---|---|---|---|---|---|---|
| weight comments | comments weight | comments weight | comments weight | weight comments | weight comments | weight comments |
| 310 g. | NTR | NTR | N | 325 g | 360 g | 400 g |

TABLE 12

30 FU/ml fluid anatoxin obtained after 3 h contact with glutaraldehyde at a final concentration of 0.00263 M and after action of lysine for 15 min at 37° C

| 1st inj. | 24h | 48h | 4 days | 5 days | 2 weeks (2nd inj.) | 3 weeks |
|---|---|---|---|---|---|---|
| weight comments | comments weight | comments weight | comments weight | weight comments | weight comments | comments weight |
| 310 g | SI | SI | VSI | 320 g | 360 g | 390 g |
| 290 g | NTR | NTR | NTR | 290 g | 340 g | 380 g |
| 295 g | NTR | NTR | NTR | 310 g | 350 g | 390 g |
| 280 g | SI | NTR | NTR | 300 g | 320 g | 350 g |
| 260 g | SI | VSI | VSI | 270 g | 290 g | 310 g |
| 310 g | NTR | VSI | NTR | 330 g | 360 g | 390 g |

TABLE 13

30 FU/ml adsorbed anatoxin obtained after 3 h contact at 37° C with glutaraldehyde to a final concentration of 0.00263 M

| 1st inj. | 24 h | 48 h | 4 days | 5 days | 2 weeks (2nd inj.) | 3 weeks |
|---|---|---|---|---|---|---|
| weight comments | comments weight | comments weight | comments eight | weight comments | weight comments | weight comments |
| 290 g | Er 14 | Er 14 | N pinkish | 320 g | 350 g  N | 365 g N |
| 280 g | Er 12 | Er 12 | N pinkish | 315 g | 340 g  N | 340 g N |
| 290 g | VSL | VSL | N pinkish | 325 g | 340 g | 400 g N |
| 270 g | SI | SI | S Er | 325 g | 350 g | 380 g NTR |
| 270 g | Er 12 | Er 12 | N pinkish | 300 g | 340 g  N | 370 g N |
| 290 g | VSL | Er 10 | SN S Er | 315 g | 380 g | 410 g SN |

TABLE 14

30 FU/ml adsorbed anatoxin obtained after 3 h contact with glutaraldehyde at a final concentration of 0.00263M and after action of lysine for 15 min at 37° C

| 1st inj. | 24 h | 48 h | 4 days | 5 days | 2 weeks (2nd inj.) | 3 weeks |
|---|---|---|---|---|---|---|
| weight comments | weight comments | weight comments | weight comments | weight comments | weight comments | weight comments |
| 300 g | Er 11 | Er 11 | N pinkish | 350 g | 370 g  N | 400 g |
| 310 g | Er 11 | Er 11 | N pinkish white | 335 g | 350 g | 360 g |
| 250 g | Er 11 | Er 11 | SN slightly pinkish | 320 g | 320 g | 350 g |
| 300 g | NTR | VSL | N | 300 g | 360 g | 400 g |
| 310 g | Er 11 | Er 11 | N pinkish | 330 g | 350 g  N | 370 g |
| 300 g | Er 20 | Er 15 | N pinkish | 325 g | 340 g  N | 390 g |

TABLE 15

Titer of antidiphtherial antibodies circulating after two vaccinal injections of fluid or adsorbed anatoxins. Anatoxins obtained after 3h incubation at 37° C with a 0.00263 M glutaraldehyde solution, the reaction being stopped by the action of lysine or by dialysis

| Time of incubation at 37° C | 30 FU/ml fluid vaccines | 30 FU/ml adsorbed vaccines |
|---|---|---|
| 3 h | 0,75 | 2 |
| 3 h + lysine 15' | 0,75 | 2,5 |

Titers are determined on mixtures of sampled blood of equal volume.

TABLE 16

Study of the vaccinating power of fluid anatoxins obtained by the action of 0.0263 H glutaraldehyde on a partially purified 2000 FU/ml diptherial toxin ($P_2$)

1. Preparation of anatoxins

| Time of contact at 37° C | Flocculation before dialysis | | Flocculation after dialysis | |
|---|---|---|---|---|
| | FU/ml | Kf | FU/ml | Kf |
| 1 mn | 1,650 | 4' | 1,200 | 4' |
| 3 h | 1,260 | 55' | 1,170 | 1 h |
| 24h | 1,060 | 1 h 30 | 1,000 | 4 h |
| 3 days | 1,000 | 24 h | 900 | 24 h |
| 1 week | 900 | 24 h | 900 | 24 h |

TABLE 17

2. Titer of circulating diphtherial antibodies expressed in International Antitoxic Units after two vaccinal injections of different anatoxins.

| Time of contact at 37° C | 30 FU/ml fluid anatoxins I.A.U./ml |
|---|---|
| 1 mn | 0,25 |
| 3 h | <0,01 |
| 24 h | <0,01 |
| 3 days | <0,01 |
| 1 week | <0,01 |

The following description also gives the results obtained with detoxification of a partially purified 2,500 FU/ml diphtherial toxin ($P_2$) by the action of glutaraldehyde at a final concentration of 0.0263 M for various times of contact. The vaccinal power of the various anatoxins thus obtained was also studied.

1°. Detoxification

The following times of contact were used: 1 min, 7 min, 20 min, 1 hr, 3 hr, 19 hr.

Table 17a shows that the toxin is already detoxified after contact for 1 minute and that its flocculating power greatly decreases as with regard to the time of contact.

2°. Flowing on a "Sephadex G 100" column.

The curve obtained after flowing 10 ml, 2,500 FU/ml diphtherial toxin $P_2$, used as control, shows a peak at tube n°26 usually corresponding to the monomer toxin.

On the other hand, after flowing 10 ml of various anatoxins on the column, peaks are observed at tubes n°16, indicating the presence of high molecular weight proteins corresponding to polymerized toxins.

The amount of polymer toxin increases with the time of contact at + 37° C.

Table 17b gives the results obtained. It is interesting to note the correlation between the results of detoxification and the degree of toxin polymerization. It is noted that the longer the duration of the reaction is, the more the amount of polymer toxin increases, whereas, to provide valid vaccines, detoxification must be stopped very quickly. Therefore, according to the invention, the degree of toxin polymerization is limited.

3°. Study on the vaccinal power of polymer peaks (tubes n° 16)

The anatoxins recovered in tubes n° 16, diluted to 30 FU/ml, are injected in the liquid form.

The anatoxins obtained after 1 min and 7 min contact with glutaraldehyde provide a higher antibody titer than the one obtained with a formolized toxin.

Titers decrease with longer contact times (table 17c)

TABLE 17a

STUDY ON THE VACCINAL POWER OF FLUID ANATOXINS, OBTAINED BY THE ACTION OF 0.0263 M GLUTARALDEHYDE FOR VARIOUS DURATIONS OF CONTACT ON A PARTIALLY PURIFIED 2,500 FU/ml DIPTHERIAL TOXIN ($P_2$)

I. Detoxification of the ($P_2$) toxin

| Time of contact at 37° C | FU/ml | Kf | Innocuity test on the guinea pig Comments after | | | | | | |
|---|---|---|---|---|---|---|---|---|---|
| | | | inj. | 2 days | 3 days | 4 days | 5 days | 6 days | 7 days |
| 1 mn | 1,600 | 3 mn | 355 | NTR | NTR | NTR | NTR | NTR | 330 |
| | | | 350 | NTR | NTR | NTR | NTR | NTR | 380 |
| 7 mn | 1,140 | 3 mn | 350 | NTR | NTR | NTR | NTR | NTR | 360 |
| | | | 375 | NTR | NTR | NTR | NTR | NTR | 400 |
| 20 mn | 875 | 3 mn | 335 | NTR | NTR | NTR | NTR | NTR | 370 |
| | | | 310 | NTR | NTR | NTR | NTR | NTR | 370 |
| 1 h | 720 | 4 mn | 345 | NTR | NTR | NTR | NTR | NTR | 360 |
| | | | 345 | NTR | NTR | NTR | NTR | NTR | 370 |
| 3 h | 525 | 5 mn | 350 | NTR | NTR | NTR | NTR | NTR | 350 |
| | | | 345 | NTR | NTR | NTR | NTR | NTR | 380 |
| 19 h | 400 | 1.5 mn | 320 | NTR | NTR | NTR | NTR | NTR | 350 |
| | | | 305 | NTR | NTR | NTR | NTR | NTR | 330 |

TABLE 17b

RESULTS OBTAINED AFTER FLOWING ON A COLUMN, OF A PARTIALLY PURIFIED 2,500 FU/ml DIPHTHERIAL TOXIN, DETOXIFIED BY THE ACTION OF 0.0263 M GLUTARALDEHYDE FOR VARIOUS TIMES OF CONTACT.

| Glutaraldehyde Duration of contact | Controls 0 | 1 mn | 7 mn | 20 mn | 1 h | 3 h | 19 h |
|---|---|---|---|---|---|---|---|
| Temperature | 0 | 37° C | 37° C | 37° C | 37° C | 37° C | 37° C |
| FU/ml | 2,500 | 1,600 | 1,140 | 875 | 720 | 525 | 400 |
| Nature of the Toxin | monomer tube n° 26 | | | Polymer (tubes n° 16) increasing amount | | | |

Table 17c
TITERS OF CIRCULATING DIPTHERIAL ANTIBODIES EXPRESSED IN INTERNATIONAL ANATOXIC UNITS AFTER TWO VACCINAL INJECTIONS OF VARIOUS ANATOXINS DILUTED TO 30 FU/ml

| ANATOXINS OBTAINED BY THE ACTION OF: | | IAU/ml |
|---|---|---|
| | 1 mn at 37° C | 1 |
| | 7 mn at 37° C | 0.50 |
| Glutaraldehyde | 20 mn at 37° C | 0.25 |
| after | 1 h at 37° C | 0.25 |
| | 3 h at 37° C | 0.25 |
| 19 h at 37° C | | 0.075 |
| Formol (control) | | 0.25 |

Detoxification of 3,000 FU/ml diphtherial toxin ($P_2$), partially purified by the action of glutaraldehyde, was also studied at variable concentrations and times of contact.

The following concentrations were used: 0.00263 M, 0.00526 M, 0.00789 M, 0.0105 M, 0.0131 M, 0.0157 M Durations of contact vary from 5 minutes to 3 hours.

Table 17d shows that detoxification is obtained after 30 minutes contact at + 37° C for 0.0157 M and 0.0131 M concentrations of glutaraldehyde, after 1 hour of contact for 0.0105 M concentration, and after 3 hours contact for 0.00789 M concentration. Samples submitted to the action of concentrations of 0.00526 M and 0.00263 M were not detoxified after contact of 3 hours.

Table 17d
DETOXIFICATION OF 3,000 FU/ml DIPHTHERIAL TOXIN ($P_2$), PARTIALLY PURIFIED BY THE ACTION OF GLUTARALDEHYDE AT VARIABLE CONCENTRATIONS AND DURATIONS OF CONTACT

| Concentrations | Durations of contact | FU/ml | TOXICITY (MONITORED ON THE GUINEA PIG) |
|---|---|---|---|
| 0.00263 M | 1 h | 2400 | Toxic |
| | 3 h | 2,200 | |
| 0.00526 M | 1 h | 2,000 | Toxic |
| | 3 h | 1,950 | |
| 0.00789 M | 15 mn | 2,200 | Toxic |
| | 1 h | 1,800 | |
| | 3 h | 1,500 | Detoxified |
| 0.0105 M | 5 mn | 2,280 | Toxic |
| | 30 mn | 1,800 | |
| | 1 h | 1,500 | Detoxified |
| 0.0131 M | 5 mn | 2,375 | Toxic |
| | 30 mn | 1,400 | |
| | 1 h | 1,350 | Detoxified |
| 0.0157 M | 5 mn | 1,800 | Toxic |
| | 30 mn | 1,290 | |
| | 1 h | 1,200 | Detoxified |

B. Study on the detoxification of purified tetanic toxin.

1. Action of glutaraldehyde on 500 FU/ml purified toxin.

Table 18 gives the results of experiments effected with a final glutaraldehyde concentration of 0.00263 M.

Complete detoxification is obtained after contact for 1 minute. It is noted a decrease in the flocculating titer greater than the one observed with a formol after a duration of contact greater than or equal to 1 hour.

2. Preparation of tetanus anatoxins by the action of glutaraldehyde or formol and comparative studies on the vaccinal powers in the fluid or adsorbed form.

The anatoxin preparations were studied after contact for 5 minutes and 1 hour with glutaraldehyde using as control an anatoxin detoxified by formol under the conventional conditions.

All 6 vaccines are very well tolerated: neither reaction nor loss of weight are observed in tested animals;.

Table 19 gives the titers of circulating antibodies.

The vaccines obtained by the action of glutaraldehyde, and notably the one obtained after contact for 5 minutes, have a higher immunological activity than those obtained by the action of formol.

Fluid or adsorbed anatoxins prepared with glutaraldehyde give practically the same immunological response, whereas the anatoxin prepared by the action of formol gives a better response than the same fluid preparation.

Detoxification of purified 525 FU/ml tetanus toxin by the action of glutaraldehyde was also studied at variable concentrations and durations of contact.

The following concentrations were used: 0.00263 M, 0.00197 M, 0.00131 M, 0.00066 M, 0.00033 M.

Table 19a shows that detoxification is obtained after 15 minutes contact at 37° C for final glutaraldehyde concentrations of 0.00263 M, and 0.00197 M, after 30 minutes contact for a concentration of 0.00131 M. Samples subjected to the action of concentrations of 0.00066 M and 0.00033 M are not detoxified even after contact for 3 hours.

TABLE 18
Detoxification of purified 500 FU/ml tetanic toxin by the action of glutaraldehyde at a final concentration of 0.00263 M

| Time of contact at 37° C | FU/ml | Kf | Injected dilutions | Innocuity test on mice* 24 h | 48 h | 72 h | comments after 6 days |
|---|---|---|---|---|---|---|---|
| 1' | 430 | 20' | 1/10 | NTR | NTR | NTR | NTR |
| 1 h | 330 | 40' | 1/100 | NTR | NTR | NTR | NTR |
| | | | 1/10 | NTR | NTR | NTR | NTR |
| 3 h | 330 | 60' | 1/100 | NTR | NTR | NTR | NTR |
| | | | 1/10 | NTR | NTR | NTR | NTR |
| 6 h | 330 | 60' | 1/100 | NTR | NTR | NTR | NTR |
| | | | 1/10 | NTR | NTR | NTR | NTR |
| 24 h | 300 | 1h10 | 1/100 | NTR | NTR | NTR | NTR |
| | | | 1/10 | NTR | NTR | NTR | NTR |
| 48 h | 300 | 1h15 | 1/100 | NTR | NTR | NTR | NTR |
| | | | 1/10 | NTR | NTR | NTR | NTR |
| 1 week | 300 | 1h15 | 1/100 | NTR | NTR | NTR | NTR |
| | | | 1/10 | NTR | NTR | NTR | NTR |
| 2 weeks | 300 | 1h15 | 1/100 | NTR | NTR | NTR | NTR |
| | | | 1/10 | NTR | NTR | NTR | NTR |
| 2 weeks | 300 | 1h15 | 1/100 | NTR | NTR | NTR | NTR |

*Intramuscular injection of 1 ml to 3 mice, after dilution to 1/10 and 1/100 with a sterile 9% solution

TABLE 19
Titer of circulating antitetanic antibodies expressed in International Antitoxic Units after two injections of fluid or adsorbed vaccinal anatoxins obtained after:

| Anatoxins obtained by the action of | 30 FU/ml fluid vaccine I.A.U./ml | 30 FU/ml adsorbed vaccine I.A.U./ml |
|---|---|---|
| (a) glutaraldehyde 5' contact | 25 | 27.5 |
| (b) glutaraldehyde (1 h contact) | 20 | 20 |

TABLE 19-continued

Titer of circulating antitetanic antibodies expressed in International Antitoxic Units after two injections of fluid or adsorbed vaccinal anatoxins obtained after:

| Anatoxins obtained by the action of | 30 FU/ml fluid vaccine I.A.U./ml | 30 FU/ml adsorbed vaccine I.A.U./ml |
|---|---|---|
| (c) formol | 2 | 8 |

(a) 5' incubation at 37° C with a 0.00263 M glutaraldehyde solution
(b) 1 h incubation at 37° C with a 0.00263 M glutaraldehyde solution
(c) 2 weeks incubation at 37° C with 2% formol.
Blood samples were taken two weeks after the second injection.
Sera from 6 vaccinated guinea pigs in each group were mixed in equal volume.

TABLE 19a

DETOXIFICATION OF PURIFIED 525 FU/ml TETANUS TOXIN BY THE ACTION OF GLUTARALDEHYDE AT VARIABLE FINAL CONCENTRATIONS AND TIMES OF CONTACT.

| Concentrations | Duration of contact | FU/ml | Toxicity (determined on mouse) |
|---|---|---|---|
| 0.00263 M | 1 mn | 470 | Toxic |
|  | 5 mn | 450 |  |
|  | 15 mn | 420 |  |
|  | 30 mn | 400 | Detoxified |
|  | 1 h | 380 |  |
|  | 3 h | 350 |  |
| 0.00197 M | 1 mn | 480 | Toxic |
|  | 5 mn | 470 |  |
|  | 15 mn | 450 |  |
|  | 30 mn | 425 | Detoxified |
|  | 1 h | 400 |  |
|  | 3 h | 390 |  |
| 0.00131 M | 5 mn | 470 | Toxic |
|  | 15 mn | 450 |  |
|  | 30 mn | 430 |  |
|  | 1 h | 425 | Detoxified |
|  | 3 h | 400 |  |
| 0.00066 M | 15 mn | 470 | Toxic |
|  | 30 mn | 470 |  |
|  | 1 h | 460 |  |
|  | 3 h | 460 |  |
| 0.00033 M | 15 mn | 470 | Toxic |
|  | 30 mn | 450 |  |
|  | 1 h | 460 |  |
|  | 3 h | 460 |  |

C. The action of glutaraldehyde on 10 CHD/ml crude α staphylococcus toxin (0.040 mg proteinic N/ml).

Tables 20 and 21 give the results obtained by the action of 0.0526 M and 0.00526 M final concentrations of glutaraldehyde.

The action of glutaraldehyde at a concentration of 0.0526 M, i.e. corresponding to the amount of formol usually used to detoxify said toxin for at least one week at 37°, induces immediate detoxification of the toxin. A complete loss of titer is observed after contact for one week at 37° C.

On the other hand, a 0.00526 M concentration does not detoxify after contact for 1 week at 37° C.

Table 22 shows that a 0.0263 M glutaraldehyde concentration is sufficient to detoxify crude toxin in 5 minutes, the titer decreasing after contact for one hour.

Table 23 shows that the titer remains unchanged when the anatoxin is held at + 4° C, in the presence of glutaraldehyde, whereas a decrease is observed with incubation at 37° C, as has been stated.

Table 24 confirms the optimum glutaraldehyde concentration of 0.0263 M to detoxify a 10 U/ml crude toxin in 5 minutes at ambient temperature, without loss of titer if the time of contact is not exceeded.

TABLE 20

Detoxification of crude α staphylococcus toxin by the action of glutaraldehyde at a final concentration of 0.0526 M

| Time of contact at 37° C | MHD/ml | CHD/ml Titer - Method | |
|---|---|---|---|
|  |  | toxin | anatoxin |
| Control | 2,048 | 10 | 10 |
| 5' | 0 | 0 | 7 |
| 1 h | 0 | 0 | 7 |
| 3 h | 0 | 0 | 5 |
| 6 h | 0 | 0 | 3 |
| 24 h | 0 | 0 | 2 |
| 4 days | 0 | 0 | 1 |
| 1 week | 0 | 0 | < 0.5 |

*Control : toxin without glutaraldehyde

TABLE 2

Detoxification of crude α toxin by the action of glutaraldehyde at a final concentration of 0.00526 M

| Time of contact at 37° C | MHD/ml | CHD/ml titer-method | |
|---|---|---|---|
|  |  | toxin | anatoxin |
| Control* | 2,048 | 10 | 10 |
| 5' | 1,024 | 10 | — |
| 1 h | 1,024 | 10 | — |
| 3 h | 512 | 8 | 8 |
| 6 h | 256 | 8 | 10 |
| 24h | 256 | 8 | 8 |
| 4 days | 256 | 8 | 8 |
| 1 week | 512 | 8 | 8 |

*Control : toxin without glutaraldehyde

TABLE 22

Detoxification of crude α toxin by the action of glutaraldehyde at a variable final concentration

| Final Concentration | Time of contact at normal temperature | MHD/ml | CHD/ml |
|---|---|---|---|
| Toxin without glutaraldehyde | — | 2,048 | 10 |
| 0.0131 M | 5' | 64 | 10 |
|  | 1 h | 32 | 10 |
| 0.0263 M | 5' | 0 | 10 |
|  | 1 h | 0 | 8 |
| 0.0394 M | 5' | 0 | 10 |
|  | 1 h | 0 | — |
| 0.0526 M | 5' | 0 | 10 |
|  | 1 h | 0 | — |

TABLE 23

Stability of the titer of a crude α toxin detoxified by glutaraldehyde at a final concentration of 0.0263 M

| Conservation | Conservation temperature | |
|---|---|---|
|  | + 4° C CHD/ml | + 37° C CHD/ml |
| 5' | 10 | 10 |
| 24 h | 10 | 6.6 |
| 3 days | 10 | — |
| 4 days | 10 | 6.6 |

TABLE 23-continued

Stability of the titer of a crude α toxin detoxified by glutaraldehyde at a final concentration of 0.0263 M

| Conservation | Conservation temperature | |
|---|---|---|
| | + 4° C CHD/ml | + 37° C CHD/ml |
| 5 days | 10 | — |
| 1 week | 10 | 5 |
| 2 weeks | 10 | 5 |
| 3 weeks | 10 | — |
| 1 month | 10 | — |

TABLE 24

Detoxification of crude α staphylococcus toxin by glutaraldehyde at variable concentration at ambient temperature.

Time of contact = 5'

| Glutaraldehyde at a final concentration of | Toxin without glutaraldehyde | 0.00526 M | 0.0131 M | 0.0263 M | 0.0394 M | 0.0526 M |
|---|---|---|---|---|---|---|
| MHD/ml | 2,048 | 1,024 | 1 28 | 0 | 0 | 0 |
| CHD/ml | 10 | 10 | 10 | 10 | 10 | 10 |

D. The action of glutaraldehyde on purified alpha staphylococcus toxin

Table 25 shows the effects of various concentrations of glutaraldehyde added to a purified α staphylococcus toxin; it is seen that a 0.00526 M concentration is the best to detoxify a 137 CHD//ml toxin (0.633 mg/ml total nitrogen).

Table 26 shows the stability of said anatoxin held at 4° C and 37° C (treated with 0.01 M concentration lysine or subjected to dialysis).

TABLE 25

Detoxification of a 137 CHD/ml purified α staphylococcus toxin (total nitrogen 0.633 mg/ml) in bicarbonate solution (1 per 10,000 merthiolate) by glutaraldehyde at variable concentrations.

| Duration of contact at ambient temperature | | 0.00131 M | 0.00263 M | 0.00526 M | 0.0131 M |
|---|---|---|---|---|---|
| <5 min | MHD/ml | ≧1,000 | 1,000 | ≧1,000 | <50 |
| 30 min | MHD/ml | ≧ 1,000 | ≧ 1,000 | ≧ 10 | < 10 |
| 1hr | MHD/ml | non detoxified | non detoxified | <4 | <4 |
| | CHD/ml | | | 138 | 66 |
| Yield efficiency | | — | — | 100% | 50% |

TABLE 26

Stability monitored on a 137 CHD/ml purified α staphylococcus toxin in 1 g/l bicarbonate solution per 0.00526M/glutaraldehyde

| | Without lysine, dialyzed against 9‰ NaCl | | After contact for 15 min at 37° C with lysine at a final concentration of 0.01M, dialyzed against 9‰ NaCl ted | |
|---|---|---|---|---|
| | 1 per 10,000 merthiolated | | | |
| After dialysis MHD/ml in vivo | <8 NTR | | <8 NTR | |
| After being held at | 4° C | 37° C | 4° C | 37° C |
| for 20 days MHD/ml in vivo | <8 NTR | <8 NTR | <8 NTR | <8 NTR |
| for 31 days MHD/ml in vivo | <8 NTR | <8 NTR | <8 NTR | <8 NTR |

E. Study of the vaccinal power of a crude staphylococcus toxin, detoxified by glytaraldehyde, then purified and adjusted to a titer equivalent to that of known formol vaccines Table 27 shows that the immunological activity of the toxin detoxified by glutaraldehyde is equal to that of the toxin detoxified by formol.

Table 28 shows the evolution of the levels of antibodies in vaccinated animals.

Table 29 shows that the immunologial activity decreases after vaccination with a crude toxin detoxified with an excess of glutaraldehyde i.e. corresponding to a 0.0526 M concentration.

TABLE 27

Comparative amounts of titers of antistaphylolysine obtained after vaccination of a rabbit with 6.6 CHD/ml purified α anatoxins.

| | Detoxification by 4.5% 0 formol + held at 37° C | Detoxification by glutaraldehyde at a final concentration of 0.0263 M, duration of contact = 5' |
|---|---|---|
| amount of antistaphylolysine in rabbit serum after three 1 ml intramuscular injections of anatoxin at 15 day intervals. | 2 J/ml | 3 U/ml |
| | 10 U/ml | 3 U/ml |
| Blood sample taken 15 days after the last injection. | 3 U/ml | 3 U/ml |

Table 28

Evolution of antibody amounts after vaccination with purified α staphylococcus anatoxins detoxified by:
1- 4.5% formol + 9 days at 37° C
2-glutaraldehyde at a final concentration of 0.0263 M and 5' contact
Titer of purified toxin = 6.6 CHD/ml.

Antistaphylolysine ratio in serum of rabbit, vaccinated with anatoxin

| Number of injections | Detoxified with formol | | | detoxified with glutaraldehyde | | |
|---|---|---|---|---|---|---|
| 0 control | <0.1 | <0.1 | <0.1 | <0.1 | <0.1 | <0.1 |
| 1 | 0.1 | 0.5 | 0.1 | 0.5 | 0.5 | 0.1 |
| 2 | 0.1 | 3 | 3 | 2 | 2 | 2 |
| 3 | 2 | 10 | 3 | 3 | 3 | 3 |

Trials were conducted under the following conditions: intramuscular injections of 1 ml vaccine to the rabbit every 15 days. Blood sample taken 15 days after each vaccination.

TABLE 29

Evolution of the antibody amounts after vaccination of the rabbit by a crude α staphylococcus anatoxin detoxified by an excess of glutaraldehyde (final concentration 0.0526 M) titer <1 CHD/ml.

| Number of injections | Antistaphylolysine ratio in CHD/ml in sera of rabbits vaccinated with anatoxin | | |
|---|---|---|---|
| 0 Control | <0.1 | <0.1 | <0.1 |
| 1 | 0.1 | 0.1 | 0.1 |
| 2 | 1 | 0.5 | 0.5 |
| 3 | 1 | 0.5 | 0.5 |

Trials were conducted under the following conditions : intramuscular injections of 1 ml vaccine to the rabbit every 15 days. Blood samples taken 15 days after each vaccination.

F. Action of glutaraldehyde on crude β staphylococcus toxin

Tables 30 and 31 relates to a 1.25 CHD/ml toxin, which is not detoxified by glutaraldehyde concentrations of 0.0526 M and 0.0131 M.

Tables 32 and 33 relate to a 6.6 CHD/ml toxin which is not detoxified by glutaraldehyde at concentrations of 0.0526 M and 0.0131 M.

Tables 34 and 35 relate to a 10 CHD/ml β toxin and a 0.0526 M and 0.0789 M concentration of glutaraldehyde. The 0.0526 M glutaraldehyde solution does not detoxify the toxin, but glutaraldehyde at 0.0789 concentration is efficacious. 10 CHD/ml β toxin is detoxified in 5 min with a 100% yield efficiency; a decrease in the titer is again observed with contact at 37° C for 24 hours.

The results of this experimentation show a close correlation between the toxin titer, the glutaraldehyde concentration and the period of contact in order to obtain complete detoxification with high yield efficiency.

The influence of the three parameters and the method of obtaining the toxin is also shown in table 36.

TABLE 30

Detoxification of crude β toxin by glutaraldehyde at a final concentration of 0.0526 M.

| Time of contact at 37° C | MHD/ml | Toxin | CHD/ml titer - method Anatoxin |
|---|---|---|---|
| Control | 128 | 1.25 | 1.25 |
| 5' | 8 | <0.7 | 0.7 |

TABLE 30-continued

Detoxification of crude β toxin by glutaraldehyde at a final concentration of 0.0526 M.

| Time of contact at 37° C | MHD/ml | Toxin | CHD/ml titer - method Anatoxin |
|---|---|---|---|
| 1 hr | 4 | <0.7 | <0.7 |
| 3 hr | 0 | <0.7 | <0.7 |
| 6 hr | 0 | — | — |
| 24 hr | 0 | — | — |
| 1 week | 0 | <0.1 | — |
| 2 weeks | 0 | <0.1 | <0.1 |

*Control: toxin without glutaraldehyde.

G. Action of glutaraldehyde on various venoms

A series of trials were conducted to discover the minimal duration of detoxification on severals venoms.

After various trials, a concentration of glutaraldehyde solution of 10.7 ml per liter of venom at a dilution of 4 g/liter physiological salt solution was used.

Under these conditions, the minimum durations of detoxification are very variable, according to the venoms.

| | |
|---|---|
| Aspis Berus Ammodytes | 2 hr30 at 37° C |
| Dendraspis | 9 hr |
| Naja Naja | 3 hr |
| Naja Melanoleuca mixture Nigricollis Haje | 3 hr |
| Bitis Gabonica mixture Lachesis Echis Carinatus | 3 hr |

SAFETY TEST

Groups of 6 mice received injections at ½ hour intervals after the addition of glutaraldehyde to the venom solution.

The product is considered to be detoxified when 4 mice out of 6 survive an intravenous injection of ½ ml at 1/10 concentration.

The action of glutaraldehyde is then blocked by mixing an equal amount of lysine solution with the anavenom.

The use of anavenoms for the hyperimmunization of horses

Horses were immunized in 1 month and with 12 injections, excellent results being obtained with the venoms: Aspis, Berus, Ammodytes, Dendraspis, Bitis Gabonica and Laschesis, according to the following procedure:
Monday; 5 ml
Wednesday; 10 ml
Friday; 15 ml
Monday; 20 ml
Wednesday; 40 ml
Friday; 60 ml + 2.5 ml Freund's adjuvant
Monday; 80 ml
Thursday 120 ml
Monday; 160 ml + 2.5 ml Freund's adjuvant
Thursday; 200 ml
Monday; 250 ml The horses were bled 8 days after the last injection.

The sera obtained in 1 month were in every way comparable with those obtained by the conventional method in 4 or 6 months.

The horses' immunity was low after treatment of one month with the anavenoms of Echis Carinatus and the various Najas, but was sufficient to enable them to support massive doses of pure venom.

Rabbit vaccination trials with Aspis Berus, Ammodytes venom

Six rabbits received intramuscular injections of 0.5 ml 4% Aspis Berus Ammodytes venom, treated as above, with glutaraldehyde and lysine.

No mechanical difficulties, or any general reactions were observed after injections in the left thigh muscles every 7 days.

A test bleeding effected 20 days after the first injection, and before the 4th injection has shown that the animals were well immunized against the three venoms.

In conclusion, the use of glutaraldehyde to detoxify snake venoms permits hyperimmunization of horses in one month instead of 4 to 6 months, required by the old methods, and enables rabbits to be vaccinated against the venom of the 3 European vipers with a few 0.5 ml injections.

TABLE 31

Detoxification of crude β toxin by the action of glutaraldehyde at a final concentration of 0.0131 M

| Time of contact at 37° C | MHD/ml | CHD/ml Titer – Method Toxin | Anatoxin |
|---|---|---|---|
| Control x | 128 | 1.25 | 1.25 |
| 5' | 128 | 1 | 1 |
| 1 h | 32 | 1.25 | 1 |
| 3 h | 32 | 1 | 1 |
| 6 h | 32 | — | — |
| 24 h | 32 | <0.7 | <0.7 |
| 1 week | 32 | <0.2 | — |
| 2 weeks | 32 | — | — | x Control : toxin without glutaraldehyde.

TABLE 32

Detoxification of crude β toxin by action of glutaraldehyde at a final concentration of 0.0526 M

| Time of contact at 37° C | MHD/ml | CHD/ml Titer – Method Toxin | Anatoxin |
|---|---|---|---|
| Control x | 4,096 | 6.6 | 6.6 |
| 5' | 128 | 3 | 3 |
| 1 h | 32 | 2 | 2 |
| 3 h | 16 | 0.8 | 0.8 |
| 6 h | 16 | — | — |
| 1 week | 2 | 0 | — |
| 2 weeks | 0 | 0 | 0 | x Control : Toxin without glutaraldehyde.

TABLE 33

Detoxification of crude β toxin by action of glutaraldehyde at a final concentration of 0.0131 M

| Time of contact at 37° C | MHD/ml | CHD/ml titer-method toxin | anatoxin |
|---|---|---|---|
| Control* | 4,096 | 6,6 | 6,6 |
| 5' | 1,024 | 5 | — |
| 1 h | 1,024 | 5 | — |
| 3 h | — | 5 | 5 |
| 6 h | 1,024 | 4 | — |
| 24 h | 1,024 | — | — |
| 1 week | 1,024 | 4 | — |
| 2 weeks | 1,024 | 2 | 2 |

*Control : toxin without glutaraldehyde.

TABLE 34

Detoxification of crude β-toxin by the action of glutaraldehyde at a final concentration of 0.0526 M

| Time of contact at 37° C | MHD/ml | CHD/ml titer-method toxin | anatoxin |
|---|---|---|---|
| Control* | 8,000 | 10 | 10 |
| 5' | 256 | 6,6 | 10 |
| 1 h | 122 | 5 | 6,6 |
| 3 h | 128 | 3 | 3 |
| 6 h | 64 | 2 | 3 |
| 24 h | 8 | <1 | <1 |

* Control : toxin without glutaraldehyde

TABLE 35

Detoxification of crude toxin by the action of glutaraldehyde at a final concentration of 0.0789 M

| Time of contact at 37° C | MHD/ml | CHD/ml titer-method toxin | anatoxin |
|---|---|---|---|
| Control* | 8,000 | 10 | 10 |
| 5' | 32 | 0 | 10 |
| 1 h | 0 | 0 | 5 |
| 3 h | 0 | 0 | 3 |
| 6 h | 0 | 0 | 1 |
| 24 h | 0 | 0 | < 0,5 |

* Control : toxin without glutaraldehyde

TABLE 36

Detoxification of crude β toxin by glutaraldehyde in less than 5 min at ambient temperature as a function of:
 the titer of the toxin
 the concentration of glutaraldehyde
 the origin of the toxin:
  either from the fermenter pH : 7.7
  or from agitated balloon-flasks pH : 7
The results are given in CHD/ml

| Glutaraldehyde at a concentration of

TABLE 37-continued

Detoxification of berus venom in a 1 mg/ml solution by the action of glutaraldehyde at final concentrations of 0.0263 M and 0.00263 M

| | Innocuity test on mice | | | | |
|---|---|---|---|---|---|
| Time of contact at 37° C | Venom + 0.0263 M M glutaraldehyde | Venom + 0.00263 M glutaraldehyde | Venom without glutaraldehyde Control I | 0.0263 M glutaraldehyde in 9%O NaCl Control II | 0.00263 M glutaraldehyde in 9%O NaCl Control III |
| 24 h | survived | survived | dead in 5' | survived | survived |
| 48 h | survived | survived | dead in 5' | survived | survived |

Injections after dilution to 1/10 to 16g and 18 g mice

TABLE 38

Detoxification of Naja Naja venom in 1 mg/ml solution by the action of glutaraldehyde at final concentrations of 0.0263 M and 0.00263 M

| | Innocuity test on mice * | | |
|---|---|---|---|
| Time of contact at 37° C | Control venom | 0.0263 M glutaraldehyde venom | 0.00263 M glutaraldehyde venom |
| 0 h | 3 dead in 6 mn 1 dead in 40 mn | 4 dead in 4 mn | 3 dead in 6 mm 1 dead in 35 mn |
| 1 h | 4 dead in 6 mn | 4 dead in 10 mn | 4 dead in 10 mn |
| 2 h | 4 dead in 5 mn | 1 dead in 30 mn | 4 dead in 14 mn |
| 3 h | 4 dead in 6 mn | survived | 3 dead in 14 mn 1 dead in 60 mn |
| 6 h | 4 dead in 6 mn | survived | 3 dead in 18 mn 1 dead in 30 mn |
| 24 h | 4 dead in 6 mn | survived | survived |
| 48 h | 4 dead in 10 mn | survived | survived |

* 0.5 ml injections of the 1/10 diluted solution to 16g and 18 g mice.

Preparation of an anti-Aspis-Berus-Ammodytes vaccine absorbed on calcium phosphate.

1. Action of glutaraldehyde

A mixture of venoms of Aspis, Berus and Ammodytes, in a 9% sodium chloride solution and each of them at a concentration of 1 mg/ml, was detoxified by 0.263 M glutaraldehyde for 3 hours at 37° C. An equal volume of 0.1 M lysine pH 6.8 - 7.00 is then added, the mixture is incubated for 15 minutes at 37° C and kept in a refrigerator for several days. After said operations the preparation has a dark yellow color.

2. Preparation of the vaccine

Merthiolate is added to 2 liters of anavenom at a rate of 2%oo, the preparation then undergoes long dialysis against a 0.07 M $Na_2HPO_4$ solution with 2%oo merthiolate and is filtered on a sterilizing filter of the Seitz type. An equal volume of filtrate is mixed with a sterile 0.07 M calcium choride solution. A vaccine, absorbed on calcium phosphate, is thus obtained, with a pH adjusted to 6.8 - 7.00.

Tests of:
sterility
nitrogen
innocuity
immunodiffusion in gelose, are effected
after the various steps of the preparation:
before dialysis agaist 0.07M $Na_2HPO_4$ solution
after dialysis against the 0.07 M $Na_2HPO_4$ solution
after filtering on a Seitz filter
final product (see tables 39 to 44)

H. Action of glutaraldehyde on α staphylococcus germs

Table 45 shows that a 0.0131 M concentration of glutaraldehyde applied for 5 min is sufficient to inactivate α staphylocuccus germs at a density of 25 NIH-.O.D.U. NTH. ODU = NIH optical density units (USA).

Table 46 shows that the agglutination rate of rabbits, vaccinated with the α germs, so inactivated, then washed with 9% NaCl and adjusted to density of 15 NIH. O.D.U., increases regularly.

Table 47 shows that said vaccination induces the same increase in the titer of antibodies as vaccination effected with heat-killed α staphylococcus germs.

TABLE 39

| Stages of vaccine preparation | Sterility | Nitrogen in mgN/ml | Immunodiffusion in gelose |
|---|---|---|---|
| After dialysis against 0.07M $Na_2HPO_4$ solution | | 0.207 | numerous lines |
| After filtration on Seitz filter | up to standard | 0.167 | numerous lines |
| Adsorbed vaccine | up to standard | | decrease in the number of lines (supernatant) |

TABLE 40

Innocuity monitoring during preparation of the antivenomous vaccine
Antivenomous vaccine + 0.05 M lysine + 2 %OO non-dialyzed merthiolate

| | Innocuity test on mice x | | | | | | | |
|---|---|---|---|---|---|---|---|---|
| Dilutions | Weight at injection | 2 days | 3 days | 4 days | 5 days | 6 days | Weight 7 days | Comments |
| Nd | 17 g | NTR | NTR | NTR | NTR | NTR | 20 g | NTR |
| | 17 g | dead | | | | | | |
| | 17 g | NTR | NTR | NTR | NTR | NTR | 21.5 g | NTR |
| | 17 g | dead | | | | | | |
| | 18 g | NTR | NTR | NTR | NTR | NTR | 23.5 g | NTR |
| | 17 g | NTR | dead | | | | | |
| 1/10 | 17 g | NTR | NTR | NTR | NTR | NTR | 25.5 g | NTR |
| | 16 g | NTR | NTR | NTR | NTR | NTR | 22 g | NTR |
| | 17 g | NTR | NTR | NTR | NTR | NTR | 25 g | NTR |
| | 18 g | NTR | NTR | NTR | NTR | NTR | 25 g | NTR |
| | 18 g | NTR | NTR | NTR | NTR | NTR | 25 g | NTR |
| | 17 g | NTR | NTR | NTR | NTR | NTR | 21.5 g | NTR | x 0.5 ml subcutaneous injection to six 17 g and 22 g mice.

TABLE 41

Antivenomous vaccine + 0.05 M lysine + 2 %oo merthiolate dialyzed against 0.07 M $Na_2HPO_4$ + 2 %oo merthiolate

| | Innocuity test on mice | | | | | | | |
|---|---|---|---|---|---|---|---|---|
| Dilutions | Weight at injection | 2 days | 3 days | 4 days | 5 days | 6 days | Weight 7 days | Comments |
| Nd | 18 g | NTR | NTR | NTR | NTR | NTR | 21.5 | NTR |
| | 17 g | NTR | NTR | NTR | NTR | NTR | 25.5 | NTR |
| | 18 g | NTR | NTR | NTR | NTR | NTR | 25 | NTR |
| | 17 g | NTR | NTR | NTR | NTR | NTR | 21 | NTR |
| | 18 g | NTR | NTR | NTR | NTR | NTR | 24.5 | NTR |
| | 16 g | NTR | NTR | NTR | NTR | NTR | 23.5 | NTR |
| 1/10 | 17 g | NTR | NTR | NTR | NTR | NTR | 25 | NTR |
| | 19 g | NTR | NTR | NTR | NTR | NTR | 26 | NTR |
| | 17 g | NTR | NTR | NTR | NTR | NTR | 24 | NTR |
| | 16 g | NTR | NTR | NTR | NTR | NTR | 20.5 | NTR |
| | 17 g | NTR | NTR | NTR | NTR | NTR | 25 | NTR |
| | 17 g | NTR | NTR | NTR | NTR | NTR | 25.5 | NTR |

TABLE 42

Antivenomous vaccine + 0.05 M lysine + 2 %oo merthiolate dialyzed against 0.07 M Na$_2$HPO$_4$ + 2 %oo merthiolate filtered on Seitz

| Dilutions | Weight of injection | Innocuity test on mice | | | | | | Weight | Comments |
|---|---|---|---|---|---|---|---|---|---|
| | | 24 h | 48 h | 72 h | 4 days | 5 days | 6 days | 7 days | |
| Nd | 21 g | NTR | NR | NTR | NTR | NTR | NTR | 27 g | NTR |
| | 21 g | NTR | NTR | NTR | NTR | NTR | NTR | 22 g | NTR |
| | 22 g | NTR | NTR | NTR | NTR | NTR | NTR | 28 g | NTR |
| | 22 g | NTR | NTR | NTR | NTR | NTR | NTR | 27 g | NTR |
| | 18 g | NTR | NTR | NTR | NTR | NTR | NTR | 23 g | NTR |
| | 21 g | NTR | NTR | NTR | NTR | NTR | NTR | 26 g | NTR |
| 1/10 | 22 g | NTR | NTR | NTR | NTR | NTR | NTR | 30 g | NTR |
| | 21 g | NTR | NTR | NTR | NTR | NTR | NTR | 23 g | NTR |
| | 22 g | NTR | NTR | NTR | NTR | NTR | NTR | 27 g | NTR |
| | 18.5 g | NTR | NTR | NTR | NTR | NTR | NTR | 18.5 g | NTR |
| | 22 g | NTR | NTR | NTR | NTR | NTR | NTR | 27 g | NTR |

TABLE 43

Adsorbed antivenomous vaccine

| Dilutions | Weight at injection | Innocuity test on mice * | | | | | Weight Comments (g) | |
|---|---|---|---|---|---|---|---|---|
| | | 2 days | 3 days | 4 days | 5 days | 6 days | 7 days | |
| Nd | 17g | NTR | NTR | NTR | NTR | NTR | 24 | NTR |
| | 17g | NTR | NTR | NTR | NTR | NTR | 25 | NTR |
| | 18g | NTR | NTR | NTR | NTR | NTR | 26 | NTR |
| | 17g | NTR | NTR | NTR | NTR | NTR | 24.5 | NTR |
| | 16g | NTR | NTR | NTR | NTR | NTR | 24 | NTR |
| | 17g | NTR | NTR | NTR | NTR | NTR | 25 | NTR |
| | 16g | NTR | NTR | NTR | NTR | NTR | 24 | NTR |
| 1/10 | 17g | NTR | NTR | NTR | NTR | NTR | 25 | NTR |
| | 17g | NTR | NTR | NTR | NTR | NTR | 23 | NTR |
| | 17g | NTR | NTR | NTR | NTR | NTR | 24.5 | NTR |
| | 16g | NTR | NTR | NTR | NTR | NTR | 25 | NTR |
| | 16g | NTR | NTR | NTR | NTR | NTR | 25 | NTR |

* 0.25 ml subcutaneous injections to six 17g to 22g mice.

TABLE 44

Adsorbed antivenomous vaccine

Innocuity test on guinea pigs *

| Weight at injection | Comments | | | | | | Weight | Comments |
|---|---|---|---|---|---|---|---|---|
| | 24 h | 48 h | 3 days | 4 days | 5 days | 6 days | 7 days | |
| 350g | NTR | NTR | NTR | NTR | NTR | NTR | 400g | NTR |
| 320g | NTR | NTR | NTR | NTR | NTR | NTR | 360g | NTR |
| 320g | NTR | NTR | NTR | NTR | NTR | NTR | 380g | NTR |
| 310g | NTR | NTR | NTR | NTR | NTR | NTR | 370g | NTR |
| 310g | NTR | NTR | NTR | NTR | NTR | NTR | 340g | NTR |
| 330g | NTR | NTR | NTR | NTR | NTR | NTR | 370g | NTR |
| 300g | NTR | NTR | NTR | NTR | NTR | NTR | 330g | NTR |
| 310g | NTR | NTR | NTR | NTR | NTR | NTR | 345g | NTR |
| 305g | NTR | NTR | NTR | NTR | NTR | NTR | 350g | NTR |
| 305g | NTR | NTR | NTR | NTR | NTR | NTR | 350g | NTR |
| 325g | NTR | NTR | NTR | NTR | NTR | NTR | 355g | NTR |
| 300g | NTR | NTR | NTR | NTR | NTR | NTR | 350g | NTR |

* 1 ml subcutaneous injection of undiluted preparation to eight≈300 g guinea pigs. The last 4 guinea pigs are controls which received no injection.

TABLE 45

Inactivation of α staphylococcus germs by glutaraldehyde

| Time of contact at 37° C | | BD = Blood dish<br>Ch = Chapmann medium<br>NB = Nutrient broth | Development of germs at 25 NIH. O.D.U. after action of glutaraldehyde at final concentration of + | | |
|---|---|---|---|---|---|
| | | | 0 (Control) | 0.0526M | 0.01310M |
| 5mn | BD | | + | 0 | 0 |
| | Ch | | + | 0 | 0 |
| | NB | | + | 0 | 0 |
| 30mn | DB | | + | 0 | 0 |
| | Ch | | + | 0 | 0 |
| | NB | | + | 0 | 0 |
| 2h | BD | | + | 0 | 0 |
| | Ch | | + | 0 | 0 |
| | NB | | + | 0 | 0 |
| 3h | BD | | + | 0 | 0 |
| | Ch | | + | 0 | 0 |
| | NB | | + | 0 | 0 |
| 24h | BD | | + | 0 | 0 |
| | Ch | | + | 0 | 0 |

TABLE 45-continued

Inactivation of α staphylococcus germs by glutaraldehyde

| Time of contact at 37° C | | BD = Blood dish<br>Ch = Chapmann medium<br>NB = Nutrient broth | Development of germs at 25 NIH. O.D.U. after action of glutaraldehyde at final concentration of + | | |
|---|---|---|---|---|---|
| | | | 0 (Control) | 0.0526M | 0.01310M |
| | NB | | + | 0 | 0 |

+ activity checked by seeding blood dish, Chapman medium and nutrient broth. Results observed after 48 h at 37° C.

TABLE 46

Vaccination with α germs, inactivated with glutaraldehyde α germs washed in 9‰ NaCl solution, inactivated by the action of glutaraldehyde for 5 min at a final concentration of 0.0131 M, washed and adjusted to an optical density of 15 NIH.O.D.U.

| Injection of | Agglutination rate of | serum from 2 rabbits |
|---|---|---|
| 0 control | 0 | 0 |
| + 0.5 ml | 1/40 | 1/10 |
| + 1ml | 1/80 | 1/20 |
| + 1ml | 1/640 | 1/640 |
| + 1ml | 1/800 | 1/1600 |
| + 1 ml | 1/800 | 1/1600 |

Injections are given intramuscularly every 15 days. Blood samples taken 15 days after each vaccination.

TABLE 47

Comparison of the levels of antibodies in rabbits vaccinated with staphylococcus germs (strain α) inactivated by heat (1 h 15 at 62° C) by the action of glutaraldehyde at a final concentration of 0.0131 M for 5 min.

| Number of injections | Agglutinating titer of sera from vaccinated rabbits | | | | | |
|---|---|---|---|---|---|---|
| | Germs inactivated by heat | | | Germs inactivated by glutaraldehyde | | |
| 0 control | 0 | 0 | 0 | 0 | 0 | 0 |
| 1-0.5 ml vaccine | 1/40 | 1/20 | 1/40 | 1/20 | 1/40 | 1/40 |
| 12-1ml vaccine | 1/80 | 1/40 | 1/80 | 1/40 | 1/80 | 1/160 |
| 3-1ml vaccine | 1/320 | 1/320 | 1/320 | 1/320 | 1/320 | 1/640 |

Intramuscular injections of an optical density of 15 NIH units are administered to rabbits every 15 days. Blood samples taken 15 days after each vaccinal injection.

Study on the inactivation of β staphylococcus germs by glutaraldehyde with regard to the concentration of glutaraldehyde,
the duration of contact,
the density of germs,
the used medium.

Vaccinal power of inactivated germs:

Tables 48 and 49 show that a concentration of 0.0131M glutaraldehyde for 5 min. or of 0.00263 M for one half hour is sufficient to inactivate β-staphylococcus germs at a density of 30 NIH.O.D.U.

Table 50 shows the proportionality of duration necessary to inactivate (at ambient temperature) β-staphylococcus germs based on final concentrations of glutaraldehyde.

Table 51 shows the action of a 0.0131 M concentration of glutaraldehyde on various densities of germs: it is seen that a duration of 15 min is sufficient to inactivate germs even at 300 NIH.O.D.U.

Table 52 shows that the presence of 0.0065 M glutaraldehyde in a culture medium inhibits staphylococcus growth. Said experiment shows the action of glutaraldehyde even in the presence of organic substances.

Table 53 shows the increase of antibodies titer in rabbits, vaccinated with β germs, inactivated with glutaraldehyde.

TABLE 48

Inactivation of β staphylococcus germs by glutaraldehyde

| Time of Contact at 37° C | BD = blood dish  Ch = Chapman medium  NB = nutrient broth | Activity of germs at 31 NIH ODU after action of glutaraldehyde at final concentrations of : (+) | | |
|---|---|---|---|---|
| | | 0 (control) | 0.0526M | 0.0131M |
| 5mn | BD | + | 0 | 0 |
| | Ch | + | 0 | 0 |
| | NB | + | 0 | 0 |
| 30mn | BD | + | 0 | 0 |
| | Ch | + | 0 | 0 |
| | NB | + | 0 | 0 |
| 2h | BD | + | 0 | 0 |
| | Ch | + | 0 | 0 |
| | NB | + | 0 | 0 |
| 3h | BD | + | 0 | 0 |
| | Ch | + | 0 | 0 |
| | NB | + | 0 | 0 |
| 24h | BD | + | 0 | 0 |
| | Ch | + | 0 | 0 |
| | NB | + | 0 | 0 |

(+) Activity checked by seeding blood dish, Chapman medium and nutrient broth. Results determined ater 48 h at 37° C

TABLE 49

Inactivation of β staphylococcus germs by the action of glutaraldehyde.

| Time of contact at 37° C | BD = blood dish  Ch = Chapman medium  NB = nutrient broth | Growth of germs at 29 O.D.NIH after the action of glutaraldehyde at final concentrations of (+) | | |
|---|---|---|---|---|
| | | 0 (Control) | 0.0131M | 0.00263M |
| <5mn | BD | + | 0 | 0 |
| | Ch | + | 0 | 0 |
| | NB | + | 0 | 0 |
| 30mn | BD | + | 0 | 0 |
| | Ch | + | 0 | 0 |
| | NB | + | 0 | 0 |
| 2h | BD | + | 0 | 0 |
| | Ch | + | 0 | 0 |
| | NB | + | 0 | 0 |

(+) Activity checked by seeding blood dish, Chapman medium and nutrient broth. Results determined after 48 h at 37° C.

TABLE 50

Inactivation of β staphylococcus germs by the action of glutaraldehyde at variable concentrations and durations

| Germs in NaCl/9‰φ 10 N.I.H. O.D.U. contact at ambient temperature | Activity of germs after the action of gluraraldehyde at final concentrations: * | | | | | | |
|---|---|---|---|---|---|---|---|
| | 0 Control | 0.031M | 0.0065M | 0.00131M | 0.00065M | 0.00013-1M | 0.000065M | 0.0000131M |
| <5 mn | + | 0 | + | + | + | + | + | + |
| 30 mn | + | 0 | 0 | + | + | + | + | + |
| 1 h | + | 0 | 0 | ± | + | + | + | + |
| 2 h | + | 0 | 0 | 0 | ± | + | + | + |
| 4 h | + | 0 | 0 | 0 | ± | + | + | + |
| 24 h | + | 0 | 0 | 0 | 0 | + | + | + |

*Activity checked by seeding in nutrient broth. Results determined after 24 h at 37° C.

TABLE 51

Study of the inactivation of β staphycoccus germs by the action of glutaraldehyde at a final concentration of 0.0131M⁼ with regard to
1°) optical density (N.I.H. units)
2°) duration of contact Checking of inactivation of nutrient broths (results determined after 48 h at 37° C)

| Duration of contact | Optical density | | | | | | |
|---|---|---|---|---|---|---|---|
| | 10 | 25 | 50 | 100 | 150 | 200 | 300 |
| Germs before contact (control) | + | + | + | + | + | + | + |
| <5 mn (18° C) | + | + | ± | + | ± | + | ± |
| 15 mn (18° C) | 0 | 0 | 0 | + | 0 | 0 | 0 |
| 30 mn (37° C) | 0 | 0 | 0 | 0 | 0 | 0 | 0 |
| 1 h (37° C) | 0 | 0 | 0 | 0 | 0 | 0 | 0 |
| 2 h (37° C) | 0 | 0 | 0 | 0 | 0 | 0 | 0 |
| 4 h (37° C) | 0 | 0 | 0 | 0 | 0 | 0 | 0 |
| Control germs after 4 h at 37° C | + | + | + | + | + | + | + |

The germs are washed and diluted by a 9‰ NaCl solution of the desired optical density

TABLE 52

Inhibition of the growth of β staphylococcus germs in culture medium nitrogen total 2.856 mg/ml by the action of glutaraldehyde

| Glutaraldehyde at a final concentration of: | Medium + glutaraldehyde NIH.O.D.U. (xx) After 18 h at 37° C | Medium + germ + glutaraldehyde NIH. O.D.U. After 18 hours at 37° C | (x) Growth |
|---|---|---|---|
| 0 (control) | 0 | 9 | + |
| 0.0004 M | 0.1 | 9 | + |
| 0.0008 M | 0.3 | 9 | + |
| 0.0016 M | 0.7 | 9 | + |
| 0.0033 M | 0.7 | 7.3 | + |
| 0.0065 M | 1.7 | 1.7 | 0 |
| 0.0131 M | 5.4 | 5.4 | 0 |
| 0.0263 M | 26.6 | 26.6 | 0 |

(x) Uniform seeding for all media
(xx) based on the broth.

TABLE 53

Evolution of the antibody levels in the rabbit, vaccinated with staphylococcus germs, inactivated by glutaraldehyde. The germs (strain β) are washed and suspended in a 9‰ NaCl solution inactivated by the action of glutaraldehyde at a final concentration of 0.0131 M and then again washed and adjusted to an optical density of 18 N I H units.

| Number of injections: | Agglutinating titer of sera from 2 rabbits | |
|---|---|---|
| 0 control | 0 | 0 |
| 1- 0.5 ml of vaccine | 1/10 | 1/40 |
| 2- 1 ml of vaccine | 1/160 | 1/40 |
| 3- 1 ml of vaccine | 1/640 | 1/160 |
| 4- 1 ml of vaccine | 1/800 | 1/320 |
| 5- 1 ml of vaccine | 1/1600 | 1/640 |
| 6- 1 ml of vaccine | — | 1/800 |
| 7- 1 ml of vaccine | — | 1/800 |

Intramuscular injections of vaccine to the rabbit every 15 days. Blood samples taken 15 days after each vaccinal injection.

I. Inactivation of a culture of whooping-cough germs.

1. Action of glutaraldehyde on strain 134 at 211 O.D.U/ml

Bacterial survival is studied after seeding on Bordet Gengou medium (table 54). The culture is completely inactivated after 1 min incubation in the presence of glutaraldehyde at a final concentration of 0.0131 M.

2. Preparation of whooping-cough vaccine by the action of glutaraldehyde or heat, and comparative study of vaccinal powers.

Vaccines are studied after the action of glutaraldehyde for 1 min at 37° C or after having remained ½ hour in a water-bath at 56° C.

Table 55 shows that heat-inctivated fluid vaccine has the best immunological activity.

In the particular example selected, too much glutaraldehyde is used for inactivation, so that the preparation, inactivated by glutaraldehyde, has lower immunological activity.

Inactivation of a culture of whooping-cough germs by the action of glutaraldehyde at final concentrations of 0.00131 M and 0.000131 M.

1. Action of glutaraldehyde

The first experiment showed that the whooping-cough culture was completely inactivated after 1 min incubation in the presence of glutaraldehyde at a final concentration of 0.0131M.

A series of experiments was conducted to study the action of glutaraldehyde at lower concentrations. Table 55a shows that the culture is also inactivated after 1 min contact with glutaraldehyde at a final concentration of 0.00131 M Table 55b, on the other hand, shows that germs are not inactivated by a 0.000131M concentration.

2. Study of vaccinal power

The immunizing power of a culture, inactivated for 1 min with a 0.00131 M concentration of glutaraldehyde, was studied with regard to the same culture, inactivated with heat under the conventional conditions. The immunizing powers are then observed to be substantially identical.

TABLE 54

Inactivation of a whooping-cough culture derived from strain 134 at 200 ODU/ml by the action of glutaraldehyde at a final concentration of 0.0131 M.

| | Development after seeding on Bordet Gengou medium | |
|---|---|---|
| Time of contact at 37° C | Before washing germs with 9‰ NaCl | After washing germs with 9‰ NaCl |
| 1 mn | 0 | 0 |
| 15 mn | 0 | 0 |
| 30 mn | 0 | 0 |
| 1 hour | 0 | 0 |
| 2 hours | 0 | 0 |
| 4 hours | 0 | 0 |
| Germs without glutaraldehyde = control | ++++ | |

TABLE 55

Titer in International Protection Units of the
preparation of fluid whooping-cough vaccine at
16 NIH units per ml (16 ODU) determined on the mouse
("Mouse protection test")
-after 1 min.contact at 37° C with a 0.0131 M
glutaraldehyde solution
-after 1/2 hour in water-bath at 56° C

| Germs inactivated with | 16 ODU/ml fluid vaccine protection units/ml |
|---|---|
| Glutaraldehyde (1 min contact) | 4.04 |
| Glutaraldehyde (1/2 hour in water-bath at 56° C) | 13.95 |

TABLE 55b

Inactivation of a 84 ODU/ml whooping-cough culture
(Q 206 S 509) by the action of glutaraldehyde at
a final concentration of 0.000131 M

| Duration of contact at 37° C | Development after seeding on BORDET-GENGOU medium |
|---|---|
| 1 mn | +++ |
| 15 mn | +++ |
| 30 mn | +++ |
| 1 hour | +++ |
| 2 hours | +++ |
| 4 hours | +++ |

TABLE 55a

Inactivation of a 84 O.D.U./ml whooping-cough
(Q 266 S-509) culture by the action of glutaraldehyde
at a final concentration of 0.00131/M

| Duration of contact at 37° C | Development after seeding on BORDET-GENGOU medium |
|---|---|
| 1 mn | 0 |
| 15 mn | 0 |
| 30 mn | 0 |
| 1 hour | 0 |
| 2 hours | 0 |
| 4 hours | 0 |
| Germs without glutaraldehyde = control | ++++ |

J. Inactivation of polyiomyelitic viruses by glutaraldehyde Three polyomyelilic viruses inactivation tests with glutaraldehyde were carried out. 1st test:

Materials and methods:
Poliomyelitic virus Type III
Glutaraldehyde: q.s. for 0.00263 M
Stoving at 37° C for 5 days (120 hrs)
Storage at + 4° C after neutralization by means of sodium bisulphite.

Comments:

a. in the hour following the introduction of glutaraldehyde, the virus suspension becomes acidic, the pH changing from 7.2 to 6.7 - 6.8.

After 24 hours, an opalescence, developing into flocculation is observed, which then gives fairly large, aggregates which sediment slowly.

b. After the addition of glutaraldehyde, the titer in 50% cytopathogenic doses (CPD 50) of the viral suspension appears to decrease in a manner directly proportional to the logarithm of the stoving time.

For a titer of $10^{7.5}$ CPD 50 per milliliter at the start, $10^{2.5}$ CPD 50 per million milliliter remain after 120 hr stoving (duration of stoving calculated for total inactivation: about 5 ½ months).

c. Inactivation checking (500 ml seeded on cellular culture dishes) : positive in 48 hours.

2nd test:
poliomyelitic virus Type III
Glutaraldehyde q.s. for 0.00526 M
stoving at 37° C for 4 days (96 hours)
storage at +4° C after neutralization with sodium bisulphite.

Comments:

a. acidification to about pH 6.5 after addition of glutaraldehyde.

Precipitation occurs slightly earlier but is much more intense; slow sedimentation of a thick layer of fibrous precipitate.

b. The inactivation curve is irregular: after a sudden drop in the first hour (reduction of 5 log) it levels off for 24 hours, a collapse being then observed at the 48th hour.

c. Inactivation checkings are, however, positive: all the cellular cultures seeded are destroyed on the 7th day).

3rd test
Mixture of equal portions of viruses of the three types of polio.
Glutaraldehyde: q.s. for 0.0035 M
Stoving at 37° C for 12 days.
Storage at +4° C after neutralization by sodium bisulfite.

Comments a. acidification and precipitation comparable to test n° 2.

b. Inactivation curve of the same aspect as in the second test, substantial reduction (about 4 log) in the first hours, levelling off from the 6th to the 24th hour, then collapse at 96 hours.

c. However, despite prolonging stoving for 8 more days, here also inactivation is not total: 40% of the cultures seeded with the finished product were positive.

It is possible to conclude from the above tests that:

1. Glutaraldehyde has a noticiable inactivation effect on poliomyelitic viruses.

2. However, its precipitating action on the proteins which are present as impurities in the medium, probably induces the formation of adsorbates and agglomerates of the virus, which prevent total inactivation.

A further test was therefore conducted, on virus purified by adsorption-elution in order to avoid the precipitations previously observed when glutaraldehyde was added to the crude virus suspension.

MATERIALS AND METHODS

Virus: Type III adsorbed on brushite. Washed with 0.1 M phosphate buffer; eluted with 0.4 M pH 7.4 disodium phosphate solution.

Stoved one night at 37° C. Glutaraldehye then added: q.s. for 0.00263 M Stoving at 37° for 120 hours. Storing at +4° after neutralization with Na Bisulphite.

Comments

The virus eluted in disodium phosphite is much more thermo-sensitive than the crude virus; stoving for one night at 37° C results in a decrease in virulence of nearly one unit (expressed by logarithm).

Glutaraldehyde, at the used concentration, has a very intense action on the purified virus; the loss of virulence being about 3.5 log in 6 minutes; and about 4.5 log in 25 minutes.

After 1.5 hours, a reduction of 6 log or more is observed, no cytopathogenic effect being discernible at a dilution of $10^{-1}$, which is cytotoxic in itself.

At the 6th hour, an opalesence is observed, which intensifies progressively. At the 24th hour, aggregates, forming a small amount of sediment, are observed.

Aggregates and opalescence are eliminated by filtration on a membrane (0.45 Nanometer) and do not reappear.

Inactivation checking, using 200 ml finished product, inoculated at a rate of 1 ml per 16 cm² cellular culture surface are negative after 16 days observation. Subcultures of said checkings are also negative.

CONCLUSIONS

1° Under the conditions of the test, the polio virus is completely inactivated.

2° Purified and mixed in a pH 7.4 phosphate solution, the virus is extremely susceptible to 0.00263 M glutaraldehyde. Many modifications can be brought to the above experiments, notably in so far as concerns the concentration of glutaraldehyde and the composition and pH of the elution liquid, to improve the method of vaccine manufacture and reduce to a minimum the risk of virus denaturation.

K. Study on the inactivation of a foot-and-mouth disease virus culture by the action of glutaraldehyde.

of glutaraldehyde solution gives strongly positive reactions.

The incubation of a glutaraldehyde solution with lysine neutralizes the dermonecrotic activity of the aldehyde°, said reaction can thus be used to neutralize excess glutaraldehyde after interaction of an antigenic preparation.

TABLE 56

Inactivation of a foot-and-mouth disease virus suspension at a final concentration of 0.00263 M

| Duration of contact at 37° C | PFU/0.1 ml* |
|---|---|
| control without glutaraldehyde | 10⁶ - 10⁷ |
| 5 mn | >100 |
| 1 hour | >100 |
| 3 hours | >100 |
| 6 hours | >100 |
| 24 hours | 1 to 5 |
| 48 hours | 1 to 5 |
| 5 days | 0 |
| 7 days | 0 |

*Plage forming units.

TABLE 57

| SAMPLES | INJECTIONS* | \multicolumn{7}{c}{Innocuity test on guinea pigs observations after} |
|---|---|---|---|---|---|---|---|---|
| | | 24 h | 48 h | 72 h | 1 week | 2 weeks | 3 weeks | 4 weeks |
| 0.0263 M glutaraldehyde solution | superficial | SES NTR | ES NTR | ES NTR | SES NTR | dead SI | NTR | NTR |
| | | NTR | NTR | NTR | NTR | NTR | NTR | NTR |
| 15 mn at 37° C | in depth | SES | ES | ES | SES | EScic | NTR | NTR |
| 0.0263 M glutaraldehyde solution + 0.1 M lysine | superficial | NTR | NTR | NTR | NTR | NTR | NTR | NTR |
| | | NTR | NTR | NTR | NTR | NTR | NTR | NTR |
| 15 mn at 37° C | in depth | NTR | NTR | NTR | NTR | NTR | NTR | NTR |
| | | NTR | NTR | NTR | NTR | NTR | NTR | NTR |
| 0.00263 M glutaraldehyde solution | superficial | NTR | NTR | NTR | NTR | NTR | NTR | NTR |
| | | VSL | VSL | SES SL | NSI | NTR | NTR | NTR |
| 15 mn at 37° C | in depth | NTR | NTR | NTR | NTR | NTR | NTR | NTR |
| | | NTR | NTR | NTR | NTR | NTR | NTR | NTR |
| 0.00263 M glutaraldehyde solution + 0.01 M lysine | superficial | NTR NTR | NTR NTR | NTR NTR | SN NTR | NTR NTR | NTR NTR | NTR |
| 15 mn at 37° C | in depth | NTR NTR | NTR NTR | NTR NTR | NTR NTR | NTR NTR | NTR NTR | NTR NTR |

*Subcutaneous injections of 0.5 ml of each preparation

The action of glutaraldehyde on foot-and-mouth disease viruses

Table 56 shows that inactivation is only complete after 5 days incubation in the presence of glutaraldehyde at a final concentration of 0.00263 M.

Study of vaccinal power

Preparations inactivated by glutaraldehyde treatment for 5 days and 7 days at 37° C were used. The preparations were diluted to 1/3 by mixing 1 volume of preparation, 1 volume of antirabic vaccine and 1 volume adjuvant. Vaccination of guinea pigs gave a neutralizing titer with respect to foot-and-mouth disease virus which is comparable to the titer obtained with a commercial vaccine of the same type.

L. Study of the proper toxicity of glutaraldehyde.

The description will be completed by the study of the toxicity inherent in glutaraldehyde.

Tables 57 and 58 give the results of innocuity tests, effected with a solution of glutaraldehyde in 9% sodium chloride at various concentrations, and after inoculation of the solutions with lysine.

The 0.1 M lysine control solution gives no intolerance reaction. But a 0.00263 M or higher concentration

TABLE 58

| | Innocuity test on guina pigs * Observations after | | |
|---|---|---|---|
| SOLUTIONS OF | 24 hours | 48 hours | 1 week |
| 0.1 M lysine 15 mn at 37° C | NTR | NTR | NTR |
| Glutaraldehyde 0.0263 M 15 mn at 37° C | NTR | NTR | NTR |
| Glutaraldehyde 0.0263 M + 0.1 M lysine 15 mn at 37° C | NTR | ES | ES |
| 0.01 M lysine 15 mn at 37° C | NTR | NTR | NTR |
| Glutaraldehyde 0.00263 M 15 mn at 37° C | VSL | NTR | N |
| | VSL | SI | N |
| Glutaraldehyde 0.00263 M + 0.01 M Lysine 15 mn at 37° C | NTR | NTR | N |
| | NTR | NTR | NTR |

* 0.5 ml subcutaneous injections of each preparation

Applicant studied the detoxification of a 50:50 mixture of 475 FU/ml diphtherial toxin and 475 FU/ml tetanus toxin by means of glutaraldehye with a final concentration of 0.00263 M and with variable durations of contact.

The detoxificaton was effected in 1% of sodium bicarbonate medium and 0.07 M sodium phosphate medium.

The used durations of contact are: 5 min.; 30 min; 1 h; 2 hrs; 3 hrs.

Tables 59 and 60 show that the detoxification of the diphtherial toxin is far better in phosphate medium than in bicarbonate medium.

Indeed it is substantially detoxified after 5 minutes contact in disodium phosphate medium and only after 3 hours contact in sodium bicarbonate.

On the contrary the medium does not affect the detoxification of the tetanus toxin.

Table 61 gives the percentages of copolymerized tetanus and diphtherial units.

It is pointed out that the tetanus toxin copolymerizes in disodium phosphate medium much more than in sodium bicarbonate medium. This difference is not observed with the diphtherial toxin.

Whatever the used medium is, the percentage of copolymerized units does not increase with regard to the duration of contact.

TABLE 59

Detoxification of a 50:50 mixture of 475 FU/ml tetanus toxin and 475 FU/ml diphtherial toxin by glutaraldehyde with a final concentration of 0.00263 M and variable durations of contact.
1 - Controls after dialysis on sample in 1% sodium bicarbonate solution.

| Duration of contact at 37° C | Test of innocuity of the rabbit + Comments 48 h after the injection | | | Innocuity test of the mouse ** | | | | | | | | |
|---|---|---|---|---|---|---|---|---|---|---|---|---|
| | | | | weight (g) 0h | Comments | | | | | | Wt. | Comments |
| | | | | | 24h | 48 h | 72 h | 96 h | 1 week | 2 weeks | | 3 weeks |
| 5mn | 1/10 | >20 | >20 | 20 | NTR | NTR | NTR | NTR | NTR | NTR | 23 | NTR |
| | 1/100 | >20 | >20 | | | | | | | | | |
| | 1/1000 | 12 | 18 | 21 | NTR | NTR | NTR | NTR | NTR | NTR | 23 | NTR |
| | 1/10,000 | tr | 14 | 21 | NTR | NTR | NTR | NTR | NTR | NTR | 24 | NTR |
| 30 mn | 1/1000 | 12 | >20 | 21.5 | NTR | NTR | NTR | NTR | NTR | NTR | 25 | NTR |
| | 1/10,000 | 0 | 0 | | | | | | | | | |
| | 1/100,000 | 0 | 0 | 21 | NTR | NTR | NTR | NTR | NTR | NTR | 28 | NTR |
| 1 h | Nd | ES | ES | 20 | NTR | NTR | NTR | NTR | NTR | NTR | 20 | NTR |
| | 1/10 | ES | ES | 22 | NTR | NTR | NTR | NTR | NTR | NTR | 33 | NTR |
| | 1/100 | 16 | 20 | 20.5 | NTR | NTR | NTR | NTR | NTR | NTR | 20 | NTR |
| | 1/1000 | tr | tr | 21.5 | NTR | NTR | NTR | NTR | NTR | NTR | 25 | NTR |
| 2h | Nd | * | >20 | 21.5 | NTR | NTR | NTR | NTR | NTR | NTR | 24 | NTR |
| | 1/10 | 13 | 16 | | | | | | | | | |
| | 1/100 | 0 | 0 | 22.5 | NTR | NTR | NTR | NTR | NTR | NTR | 28 | NTR |
| | 1/1000 | 0 | 0 | | | | | | | | | |
| 3h | Nd | 13/14 | 18/19 | 21.5 | NTR | NTR | NTR | NTR | NTR | NTR | 26 | NTR |
| | 1.10 | tr | 0 | 22.5 | NTR | NTR | NTR | NTR | NTR | NTR | 30 | NTR |
| | 1/100 | 0 | 0 | 22.5 | NTR | NTR | NTR | NTR | NTR | NTR | 30 | NTR |
| | 1.1000 | 0 | 0 | | | | | | | | | |
| | | | | 22 | NTR | NTR | NTR | NTR | NTR | NTR | 30 | NTR |

*0.1 ml injection of different dilutions subcutaneous to two rabbits
**1 ml injection to three mice. Diameter of reactions by the rabbit in mm — ES = eschar — tr = traces

TABLE 60

2. Controls after dialysis on the sample in 0.07 disodium phosphate solution

| Duration of contact at 37° C | Innocuity test the rabbit Comments 48 h after injection | | | Weight (g) OH | Innocuity test on the mouse | | | | | | (g) Weight | Comments |
|---|---|---|---|---|---|---|---|---|---|---|---|---|
| | | | | | Comments | | | | | | | |
| | | | | | 24 h | 48 h | 72 h | 96 h | 1 week | 2 weeks | | 3 weeks |
| 5 mn | Nd | 17 | 13 | 22 | NTR | NTR | NTR | NTR | NTR | NTR | 26 | NTR |
| | 1/10 | tr | 0 | | | | | | | | | |
| | 1/100 | 0 | 0 | 21.5 | NTR | NTR | NTR | NTR | NTR | NTR | 28 | NTR |
| | 1/1000 | 0 | 0 | | | | | | | | | |
| 30 mn | | | | 22 | NTR | NTR | NTR | NTR | NTR | NTR | 28 | NTR |
| | Nd | 13/14 | 12 | 22 | NTR | NTR | NTR | NTR | NTR | NTR | 24 | NTR |
| | 1/10 | 0 | 0 | | | | | | | | | |
| | 1/100 | 0 | 0 | 22.5 | NTR | NTR | NTR | NTR | NTR | NTR | 26 | NTR |
| | 1/100 | 0 | 0 | | | | | | | | | |
| 1 hr | | | | 21.5 | NTR | NTR | NTR | NTR | NTR | NTR | 28 | NTR |
| | Nd | 0 | 12 | 22.5 | NTR | NTR | NTR | NTR | NTR | NTR | 24 | NTR |
| | 1/10 | 0 | 0 | | | | | | | | | |
| | 1/100 | 0 | 0 | 21.5 | NTR | NTR | NTR | NTR | NTR | NTR | 22 | NTR |
| | 1/100 | 0 | 0 | | | | | | | | | |
| 2 hr | | | | 22.5 | NTR | NTR | NTR | NTR | NTR | NTR | 31 | NTR |
| | Nd | 9 | 11 | 21 | NTR | NTR | NTR | NTR | NTR | NTR | 22 | NTR |
| | 1/10 | 0 | 0 | | | | | | | | | |
| | 1/100 | 0 | 0 | 21.5 | NTR | NTR | NTR | NTR | NTR | NTR | 26 | NTR |
| | 1/1000 | 0 | 0 | | | | | | | | | |
| 3 hr | | | | 21.5 | NTR | NTR | NTR | NTR | NTR | NTR | 28 | NTR |
| | Nd | 9 | 11 | 22 | NTR | NTR | NTR | NTR | NTR | NTR | 25 | NTR |
| | 1/10 | 0 | 0 | | | | | | | | | |
| | 1/100 | 0 | 0 | 22.5 | NTR | NTR | NTR | NTR | NTR | NTR | 29 | NTR |
| | 1/1000 | 0 | 0 | | | | | | | | | |
| | | | | 21 | NTR | NTR | NTR | NTR | NTR | NTR | 26 | NTR |

TABLE 61

Tetanus and diphtherial units forming copolymers after detoxification of a 50:50 mixture of 475 FU diphtherial toxin and of 475 FU/ml tetanus toxin

| Duration of contact at 37° C | in 0.07 M disodium phosphate solution | | Copolymerized tetanus units expressed in % after precipitation by a purified antidiphtherial serum | In 1%o sodium bicarbonate solution | |
|---|---|---|---|---|---|
| | Copolymerized diphtherial units expressed in % after precipitation by an antitetanic serum | | | Copolymerized diphtherial Units in % after precipitation by a purified antitetanic serum | Copolymerized tetanus units in % after precipitation by a purified antidiphtharial serum |
| | purified | non purified | | | |
| 5 mn | 21.1 | 27.7 | 70.6 | 18.1 | 13.9 |
| 30 mn | 20 | 32.4 | 69.7 | 15.2 | 22.5 |
| 1 h | 18.2 | 18.6 | 71.5 | 18.2 | 26.7 |
| 2 h | 16.7 | 18.6 | 66.2 | 16.2 | 25 |
| 3 h | 23 | 18.6 | 66.7 | 18.2 | 18.9 |

What we claim is:

1. An improvement in a process for preparing a bacterial vaccine by reacting whole bacteria with an inactivating agent and stopping the reaction as soon as said inactivation is achieved, wherein the improvement comprises the step of inactivating the whole bacteria with glutaraldehyde as the inactivating agent at a concentration ranging from about 0.00131 M to 0.0526 M, whereby an inactivated product is obtained which is usable as a bacterial vaccine while remaining antigenic and retaining its immunizing power.

2. A process according to claim 1, wherein said bacteria are whooping cough bacteria and inactivation is almost immediate.

3. A process according to claim 1, wherein said bacteria are α-staphylococcus bacteria.

4. A process according to claim 1, wherein said bacteria are staphylococcus bacteria and inactivation is complete within about 2 hours.

5. A process according to claim 1, wherein the glutaraldehye and said bacteria are brought into contact at a temperature of from ambient temperature to about 40° C.

6. A process according to claim 5, wherein said temperature is between 35° and 40° C.

7. A process according to claim 6, wherein said temperature is about 37° C.

8. A process according to claim 1, wherein the reaction between said bacteria and glutaraldehyde is stopped by the addition of an agent able to block the glutaraldehyde-antigen reaction or to react with the glutaraldehyde which is in the free state in the reaction medium and selected from the group consisting of amino-acids and inorganic salts.

9. A process according to claim 8, wherein said agent is an amino-acid.

10. A process according to claim 9, wherein said amino-acid is lysine or glycin.

11. A process according to claim 8, wherein said agent is sodium bisulfite.

12. A process according to claim 1, wherein said reaction is stopped by subjecting the detoxified product to dialysis against an aqueous solution of an inorganic salt, whereby a fluid product usable as a bacterial vaccine is obtained.

13. A process according to claim 8, wherein said agent is an inorganic salt selected from the group consisting of sodium phosphate and sodium chloride.

14. A process according to claim 12, wherein merthiolate is added to said aqueous solution used for said dialysis.

15. A process according to claim 1, wherein said reaction is stopped by centrifuging and washing the detoxified product to remove from it the excess of glutaraldehyde.

16. A process according to claim 1, wherein a sterile calcium chloride solution is added to the detoxified product obtained in fluid form by dialysis against a buffer solution, whereby an adsorbed product useful as a bacterial vaccine is obtained.

17. A process according to claim 12, wherein aluminum hydroxide is added to said detoxified bacterial vaccine, obtained by dialysis against a sodium chloride solution, whereby an adsorbed product useful as a bacterial vaccine is obtained.

18. A process according to claim 12, wherein aluminum phosphate is added to said detoxified bacterial vaccine, obtained by dialysis against a sodium chloride solution, whereby an adsorbed product useful as a bacterial vaccine is obtained.

19. A bacterial vaccine obtained by the process according to claim 1 and containing detoxified derivatives corresponding to the toxic products of whole bacterial selected from the group consisting of whooping cough bacteria and α- and β-staphylococcus bacteria.

20. A bacterial vaccine according to claim 19, further containing an agent selected from the group consisting of amino-acids and inorganic salts.

21. A bacterial vaccine according to claim 20, wherein said agent is an amino-acid.

22. A bacterial vaccine according to claim 20, wherein said agent is selected from the group consisting of lysine and glycin.

23. A bacterial vaccine according to claim 19, in the fluid form.

24. A bacterial vaccine according to claim 19, in the adsorbed form.

25. A bacterial vaccine according to claim 21, adsorbed on calcium phosphate, aluminum hydroxide or aluminum phosphate.

26. Mixed bacterial vaccine according to claim 19 containing detoxified derivatives of at least two whole bacteria.

* * * * *

UNITED STATES PATENT AND TRADEMARK OFFICE
CERTIFICATE OF CORRECTION

PATENT NO. : 4,075,321
DATED : February 21, 1978
INVENTOR(S): Edgar Hans Relyveld It is certified that error appears in the above-identified patent and that said Letters Patent are hereby corrected as shown below:

Column 41, lines 38-39, cancel "glutaraldehye" and substitute therefor --glutaraldehyde-- .

Column 42, line 42, cancel "bacterial" and substitute therefor -- bacteria -- .

Signed and Sealed this

Twenty-eighth Day of November 1978

[SEAL]

Attest:

RUTH C. MASON
Attesting Officer

DONALD W. BANNER
Commissioner of Patents and Trademarks